(12) United States Patent
Renga et al.

(10) Patent No.: US 8,252,938 B2
(45) Date of Patent: Aug. 28, 2012

(54) PROCESS FOR THE PREPARATION OF 6-(ARYL)-4-AMINOPICOLINATES

(75) Inventors: James M. Renga, Indianapolis, IN (US); Gregory T. Whiteker, Carmel, IN (US); Kim E. Arndt, Carmel, IN (US); Christian T. Lowe, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 262 days.

(21) Appl. No.: 12/795,184

(22) Filed: Jun. 7, 2010

(65) Prior Publication Data
US 2010/0311981 A1     Dec. 9, 2010

Related U.S. Application Data

(60) Provisional application No. 61/184,874, filed on Jun. 8, 2009.

(51) Int. Cl.
*C07D 213/803* (2006.01)
(52) U.S. Cl. ...................................... 546/310
(58) Field of Classification Search .................. None
See application file for complete search history.

(56) References Cited

U.S. PATENT DOCUMENTS

| 6,784,137 B2 | 8/2004 | Balko et al. |
| 7,314,849 B2 | 1/2008 | Balko et al. |

FOREIGN PATENT DOCUMENTS

| WO | WO2007/082098 A2 | 7/2007 |
| WO | WO 2010/144380 | 12/2010 |
| WO | WO2010/144380 | 12/2010 |

OTHER PUBLICATIONS

Kazuhiro Yoshida, Fumihiro Kawagoe, Kazushi Hayashi, Shingo Horiuchi, Tsuneo Imamoto and Akira Yanagisawa: "Synthesis of 3-Hydroxypyridines Using Ruthenium-Catalyzed Ring-Closing Olefin Matathesis" Organic Letters, vol. 11, No. 3, Dec. 31, 2008.
U.S. Appl. No. 12/795,416, Applicant: James M. Renga, et al., which was filed concurrently with this application on Jun. 7, 2010.

*Primary Examiner* — Zinna Northington Davis
(74) *Attorney, Agent, or Firm* — Robert Chang; Craig E. Mixan

(57) ABSTRACT

3-Halo-6-(aryl)-4-iminotetrahydropicolinic acid esters are heated with polar solvents to prepare 6-(aryl)-4-aminopicolinates.

3 Claims, No Drawings

PROCESS FOR THE PREPARATION OF 6-(ARYL)-4-AMINOPICOLINATES

This application claims benefit of 61/184,874 filed Jun. 8, 2009.

FIELD OF THE INVENTION

The present invention concerns a process for the preparation of 6-(aryl)-4-aminopicolinates. More particularly, the present invention concerns a process for the preparation of 6-(aryl)-4-aminopicolinates from the corresponding 3-halo-6-(aryl)-4-iminotetrahydropicolinates.

BACKGROUND OF THE INVENTION

U.S. Pat. Nos. 6,784,137(B2) and 7,314,849(B2) describe certain 6-(aryl)-4-aminopicolinate compounds and their use as herbicides. Both of these patents describe the manufacture of 6-(aryl)-4-aminopicolinates from picolines having either a facile leaving group or a metal derivative in the 6-position of the picoline ring. It would be advantageous to produce 6-(aryl)-4-aminopicolinates efficiently and in high yield from a non-pyridine source.

SUMMARY OF THE INVENTION

The present invention concerns a process for the preparation of 6-(aryl)-4-aminopicolinates from the corresponding 3-halo-6-(aryl)-4-iminotetrahydropicolinates. More particularly, the present invention concerns a process for the preparation of a 6-(aryl)-4-aminopicolinate of the formula

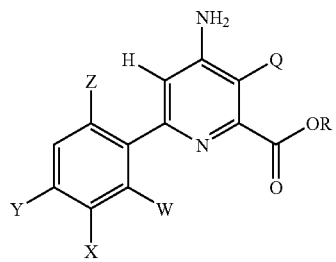

wherein
Q represents Cl or Br;
R represents $C_1$-$C_4$ alkyl; and
W represents H, F or Cl;
X represents H, F, $C_1$ or $C_1$-$C_4$ alkoxy;
Y represents halogen; and
Z represents H or F;
which comprises heating a 3-halo-6-(aryl)-4-iminotetrahydropicolinic acid ester of Formula (I)

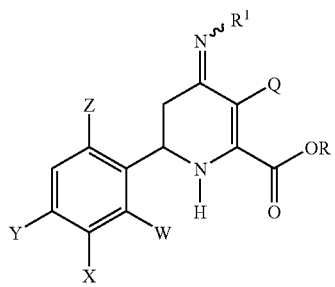

wherein
R represents $C_1$-$C_4$ alkyl;
$R^1$ represents —OS(O)$_2R^2$, —OC(O)$R^2$ or —OC(O)O$R^2$;

$R^2$ represents $C_1$-$C_4$ alkyl or unsubstituted or substituted phenyl;
Q represents Cl or Br; and
W represents H, F or Cl;
X represents H, F, $C_1$ or $C_1$-$C_4$ alkoxy;
Y represents halogen; and
Z represents H or F;
at a temperature from about 25° C. to about 150° C. in the presence of a polar solvent and recovering the product.

DETAILED DESCRIPTION OF THE INVENTION

The term "alkyl," as well as derivative terms such as "alkanoic," as used herein, include within their scope straight chain, branched chain and cyclic moieties.

The 3-halo-6-(aryl)-4-iminotetrahydropicolinate starting materials can be prepared in a number of ways. In step a of Scheme I, an aromatic aldehyde of Formula II, wherein W, X, Y and Z are as previously defined, can be condensed with a ketone, such as acetone, in the presence of a base, such as sodium hydroxide, to provide the α,β-unsaturated ketone of Formula III. These compounds can then be allowed to react with a base, such as sodium ethoxide, in the presence of a dialkyl oxalate to generate the β-diketoester of Formula IV as in step b, wherein R represents $C_1$-$C_4$ alkyl, such as in U.S. Pat. No. 4,304,728. In step c of Scheme I, reaction of an amine source, such as ammonium acetate, with compounds of Formula IV results in the formation of an enamine of Formula V. Approximately a 1:2 ratio of the β-diketoester of Formula IV to the amine source is required in the reaction. The reaction is conducted at temperatures from about 25° C. to about 80° C. Temperatures from about 60° C. to about 80° C. are generally preferred. The reaction is preferably conducted in a polar protic solvent. Preferred solvents include alcohols. Either methyl alcohol or ethyl alcohol is the most preferred solvent. Finally, in step d of Scheme I, the 4-oxo-tetrahydropicolinates of Formula VI are formed via heating of compounds of Formula V at high temperatures in a pressure vessel. The reaction is conducted at temperatures from about 125° C. to about 200° C. Temperatures from about 150° C. to about 200° C. are generally preferred. The reaction is preferably conducted in a polar aprotic solvent. Preferred solvents include ethers, such as 1,4-dioxane.

Scheme I

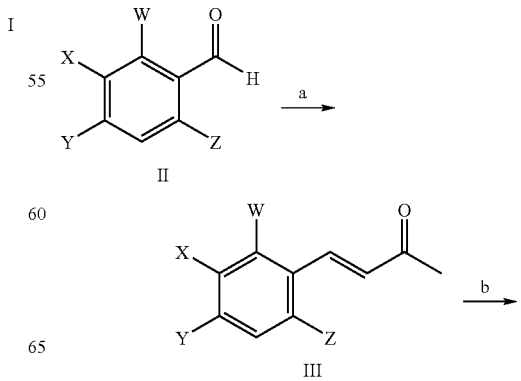

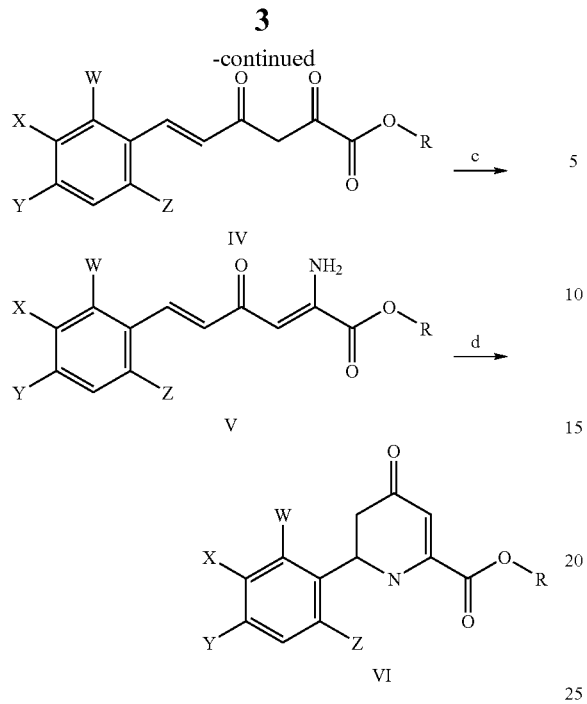

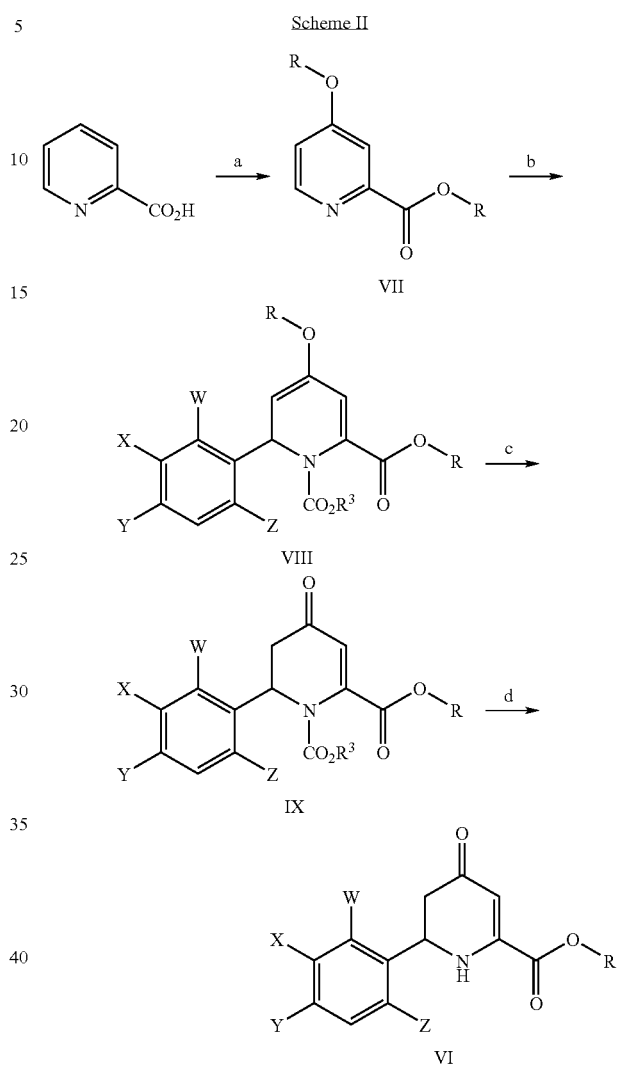

Another way to generate 4-oxo-tetrahydropicolinates of Formula VI can be found in Scheme II. In step a of Scheme II, a 2-picolinic acid is treated with thionyl chloride and an alcohol, such as methyl alcohol, to provide the 4-alkoxy-2-picolinic acid ester of Formula VII wherein R is as previously defined. Treatment of the compounds of Formula VII with a chloroformate, followed by in situ addition of an aryl zinc halide wherein W, X, Y and Z are as previously defined, to the resulting mixture affords the dihydropicolinate of Formula VIII as shown in step b, wherein $R^3$ represents phenyl. In the first part of this two step one pot protocol, a slight excess of the chloroformate over the compound of Formula VII is required.

The reaction is conducted at temperatures from about −5° C. to about 20° C. Temperatures from about −5° C. to about 10° C. are generally preferred. The reaction is preferably conducted in a polar aprotic solvent. Preferred solvents include ethers. Either tetrahydrofuran (THF) or diethyl ether is the most preferred solvent. In the second part of this step, a slight excess of the aryl zinc halide over the compound of Formula VII is required and the reaction is conducted at temperatures from about −5° C. to about 30° C. Temperatures from about 20° C. to about 30° C. are generally preferred. In step c of Scheme II, acidic hydrolysis of compounds of Formula VIII in a polar aprotic solvent, such as THF, provides the 4-oxo-tetrahydropicolinate of Formula IX protected as the carbamate. An excess of the acid over the compound of Formula VIII is required in the reaction. The reaction is conducted at temperatures from about −5° C. to about 30° C. Temperatures from about 20° C. to about 30° C. are generally preferred. The reaction is preferably conducted in polar solvent mixtures. Preferred solvents include ether-water mixtures, such as THF-water. Lastly, in step d of Scheme II, treatment of compounds of Formula IX with a base, such as sodium methoxide, followed by an aqueous workup affords the 4-oxo-tetrahydropicolinate of Formula VI. A slight excess of the base over the compound of Formula IX is required in the reaction. The reaction is conducted at temperatures from about −5° C. to about 20° C. Temperatures from about −5° C. to about 10° C. are generally preferred. The reaction is preferably conducted in a polar protic solvent. Preferred solvents include alcohols, such as methyl alcohol.

The compounds of Formula VI, wherein W, X, Y, Z and R are as previously defined, can be converted to the corresponding oximes of Formula X by reaction with hydroxylamine or hydroxylamine hydrochloride in the presence of a base, such as pyridine, and in a solvent, such as toluene or methanol, as in step a of Scheme III. An excess of the hydroxylamine over the compound of Formula VI is required in the reaction. The reaction is conducted at temperatures from about 25° C. to about 80° C. Temperatures from about 60° C. to about 80° C. are generally preferred. The reaction is preferably conducted in a polar protic solvent. Preferred solvents include alcohols. Either methyl alcohol or ethyl alcohol is the most preferred solvent. In step b of Scheme III, the oximes of Formula X can be treated with a sulfonyl chloride, acyl chloride, alkyl chloroformate or aryl chloroformate in the presence of a base to provide the corresponding sulfonylated, acylated or carbonate-containing oximes of Formula XI, where $R^1$ represents —OS(O)$_2R^2$, —OC(O)$R^2$ and —OC(O)O$R^2$, $R^2$ represents $C_1$-$C_4$ alkyl or unsubstituted or substituted phenyl and R is as previously defined. An almost 2:1 ratio of the sulfonylating, acylating or carbonylating reagent over the compound of Formula X is required in the reaction. At least one equivalent of a tertiary amine base is required, with between 1 and about 2 equivalents being preferred. The reaction is conducted at temperatures from about −5° C. to about 30° C. Temperatures from about −5° C. to about 20° C. are generally preferred. Preferred solvents include inert solvents, such as chlorinated hydrocarbons. Reaction of the substituted oximes of Formula XI with a chlorinating agent, such as sulfuryl chloride, or a brominating agent, such as bromine or N-bromosuccinimide, affords the 3-halo-(6-aryl)-4-iminotetrahydropicolinates of Formula I, wherein Q is as previously defined, as shown in step c of Scheme III. Approximately equimolar quantities of the chlorinating or brominating agent and the compound of Formula XI are required in the reaction. The reaction is conducted at temperatures from about −5° C. to about 30° C. Temperatures from about −5° C. to about 20° C. are generally preferred. Preferred solvents include inert solvents such as dichloromethane. Alternatively, formation of compounds of Formula I can be accomplished by treating compounds of Formula VI in a different order—steps c, a and then b.

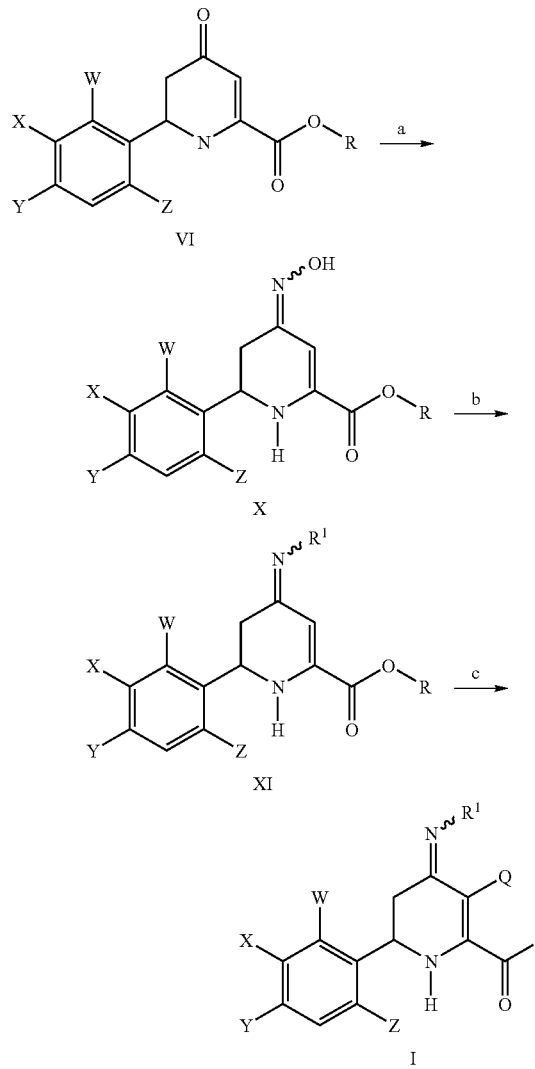

Scheme III

The 3-halo-6-(aryl)-4-iminotetrahydropicolinate starting materials, obtained by any of these processes, can be recovered by conventional means.

6-(Aryl)-4-aminopicolinate herbicides

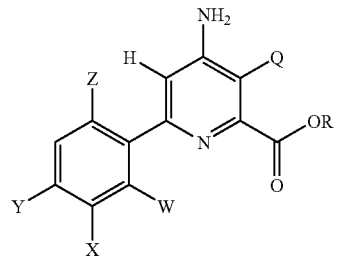

are conveniently prepared by heating 3-halo-6-(aryl)-4-iminotetrahydropicolinates

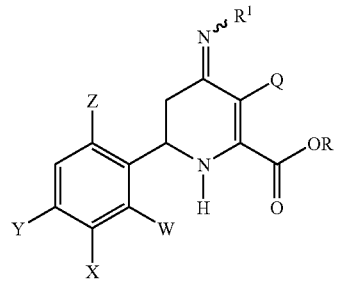

in the presence of a polar solvent. The polar solvent is preferably used in a large molar excess. The polar solvent may be either a polar protic solvent or a polar aprotic solvent. Polar protic solvents include alkanoic acids with $C_1$-$C_4$ alkanoic acid being preferred and with glacial acetic acid being most preferred. Polar aprotic solvents include amides, like N,N-dimethylformamide, N,N-dimethylacetamide or N-methyl-2-pyrrolidinone, and sulfoxides, like dimethyl sulfoxide. Optionally, a cosolvent can be used with the polar solvent. The cosolvent should be miscible with the polar solvent and the 3-halo-6-(aryl)-4-imino-tetrahydropicolinate starting material.

The conversion of the 3-halo-6-(aryl)-4-iminotetrahydropicolinate to the 6-(aryl)-4-aminopicolinate is conducted at a temperature from about 25° C. to about 150° C. The preferred temperature range is from about 25° C. to about 90° C.

It is often convenient to prepare the 3-halo-6-(aryl)-4-iminotetrahydropicolinic acid ester by chlorinating or brominating a sulfonylated, acylated or carbonate-containing oxime of the formula

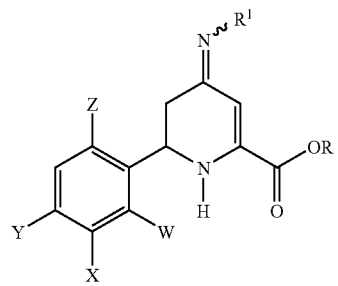

wherein W, X, Y, Z, R, $R^1$ and $R^2$ are as previously defined with a chlorinating or brominating agent. Typical chlorinating and brominating agents include chlorine, sulfuryl chloride, N-chlorosuccinimide, bromine, sulfuryl bromide and N-bromosuccinimide. Approximately equimolar quantities of the chlorinating or brominating agent are required in the reaction. The reaction is typically conducted at temperatures from about −5° C. to about 30° C. Temperatures from about −5° C. to about 20° C. are generally preferred. Preferred solvents include inert solvents such as dichloromethane.

The products obtained by any of these processes, can be recovered by conventional means, such as evaporation or extraction, and can be purified by standard procedures, such as by recrystallization or chromatography.

The following examples are presented to illustrate the invention.

EXAMPLES

Example 1

Preparation of (E)-4-(4-chloro-2-fluorophenyl)-but-3-en-2-one (1)

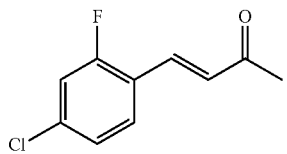

To a mechanically stirred solution of 4-chloro-2-fluorobenzaldehyde (23.8 grams (g), 0.15 mole (mol)) in acetone (100 milliliters (mL)) at room temperature was added over 20 minutes (min) a solution of sodium hydroxide (NaOH, 6.6 g, 0.165 mol) in water ($H_2O$, 400 mL). After stirring the reaction mixture overnight, dichloromethane ($CH_2Cl_2$, 100 mL) was added. The aqueous layer was separated and extracted with $CH_2Cl_2$ (100 mL), and the combined organic extracts were washed with brine and dried over magnesium sulfate ($MgSO_4$). Solvent removal followed by Kugelrohr distillation gave 4-(4-chloro-2-fluorophenyl)-3-buten-2-one (1; 22.5 g, 76%) as a colorless liquid, which solidified upon standing: by 70-80° C., 0.1 mmHg (13.33 pascals (Pa)); $^1$H NMR (400 MHz, $CDCl_3$) δ 7.59 (d, J=16.5 Hz, 1H), 7.50 (t, J=8.1 Hz, 1H), 7.22-7.12 (m, 2H), 6.76 (d, J=16.5 Hz, 1H), 2.39 (s, 3H); HRMS-ESI (m/z): calcd for $C_{10}H_8ClFO$, 198.024. found 198.025.

(E)-4-(4-Chloro-2-fluoro-3-methoxyphenyl)-but-3-en-2-one (2)

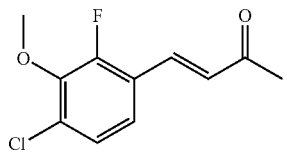

Using the procedure of Example 1,4-chloro-2-fluoro-3-methoxy-benzaldehyde (200 g, 1.6 mol), NaOH (46.6 g, 1.16 mol) and acetone (1 L) were reacted to give (E)-4-(4-chloro-2-fluoro-3-methoxyphenyl)-3-buten-2-one (2; 180 g, 74%, 93% pure by HPLC) as a pale brown liquid: $^1$H NMR (400 MHz, $CDCl_3$) δ 7.59 (d, J=16.5 Hz, 1H), 7.50 (t, J=8.1 Hz, 1H), 7.26-7.07 (m, 2H), 6.76 (d, J=16.5 Hz, 1H), 2.39 (s, 3H); HRMS-ESI (m/z): calcd for $C_{11}H_{10}ClFO_2$, 228.035. found, 228.036.

Example 2

Preparation of (E)-6-(4-chloro-2-fluorophenyl)-2,4-dioxo-hex-5-enoic acid ethyl ester (3)

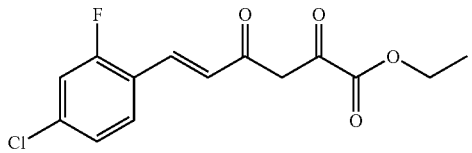

Sodium pellets (2.88 g, 0.125 mol) were slowly added to absolute ethyl alcohol (EtOH, 125 mL). After the sodium had reacted, the solvent was removed under reduced pressure, and anhydrous ether (200 mL) was added. The reaction mixture was cooled to −5° C., and a solution of (E)-4-(4-chloro-2-fluorophenyl)-but-3-en-2-one (1; 24.75 g, 0.125 mol) and diethyl oxalate (21.9 g, 0.15 mol) in anhydrous ether (25 mL) was added over 30 min. After stirring 2 days (d) at room temperature, the yellow solid was filtered and washed with ether. After 1 hour (h) of drying at room temperature, the solid was partitioned between $CH_2Cl_2$ (200 mL) and 1 N sulfuric acid ($H_2SO_4$, 150 mL). The organic layer was dried ($MgSO_4$), and the solvent was removed to give (E)-6-(4-chloro-2-fluoro-phenyl)-2,4-dioxo-hex-5-enoic acid ethyl ester (3; 32.3 g, 86%) as a yellow solid. A small sample was recrystallized from EtOH to yield yellow crystals: mp 84-85° C.; $^1$H NMR (400 MHz, $CDCl_3$) δ 14.72 (s, 1H), 7.76 (d, J=16.1 Hz, 1H), 7.49 (d, J=8.3 Hz, 1H), 7.24-7.12 (m, 2H), 6.73 (d, J=16.1 Hz, 1H), 6.53 (s, 1H), 4.38 (q, J=7.1 Hz, 2H), 1.40 (t, J=7.1 Hz, 3H); HRMS-ESI (m/z): calcd for $C_{14}H_{12}ClFO_4$, 298.041. found, 298.041.

(E)-6-(4-Chlorophenyl)-2,4-dioxo-hex-5-enoic acid ethyl ester (4)

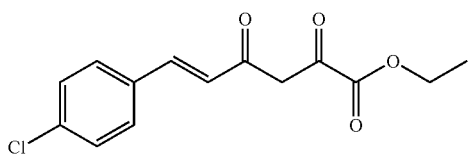

Using the procedure of Example 2, sodium pellets (6.33 g, 0.275 mol), (E)-4-(4-chlorophenyl)-but-3-en-2-one (45.16 g, 0.25 mol) and diethyl oxalate (43.8 g, 0.30 mol) were reacted to give (E)-6-(4-chlorophenyl-2,4-dioxo-hex-5-enoic acid ethyl ester (4; 61.1 g, 87%) as yellow crystals: mp 117-118° C.; $^1$H NMR (400 MHz, $CDCl_3$) δ 14.80 (s, 1H), 7.68 (d, J=15.9 Hz, 1H), 7.53-7.35 (m, 4H), 6.62 (d, J=15.9 Hz, 1H), 6.53 (s, 1H), 4.38 (q, J=7.2 Hz, 2H), 1.40 (t, J=7.1 Hz, 3H); HRMS-ESI (m/z): calcd for $C_{14}H_{13}ClO_4$, 280.050. found, 280.050.

(E)-6-(4-Chloro-2-fluoro-3-methoxyphenyl)-2,4-dioxo-hex-5-enoic acid ethyl ester (5)

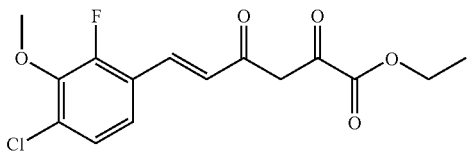

Using the procedure of Example 2, sodium pellets (5.52 g, 0.24 mol), (E)-4-(4-chloro-2-fluoro-3-methoxyphenyl)-but-3-en-2-one (2; 45.73 g, 0.20 mol) and diethyl oxalate (36.54 g, 0.25 mol) were reacted to give (E)-6-(4-chloro-2-fluoro-3-methoxyphenyl-2,4-dioxo-hex-5-enoic acid ethyl ester (5; 61.1 g, 93%) as yellow crystals: mp 67.5-69° C.; $^1$H NMR (400 MHz, CDCl$_3$) δ 14.71 (s, 1H), 7.78 (d, J=16.1 Hz, 1H), 7.27-7.18 (m, 2H), 6.73 (d, J=16.1 Hz, 1H), 6.54 (s, 1H), 4.38 (q, J=7.1 Hz, 2H), 3.99 (d, J=1.2 Hz, 3H), 1.41 (t, J=7.1 Hz, 3H); HRMS-ESI (m/z): calcd for C$_{15}$H$_{14}$ClFNO$_5$, 328.051. found, 328.051.

Example 3

Preparation of (E)-6-(4-chlorophenyl)-2,4-dioxo-hex-5-enoic acid methyl ester (6)

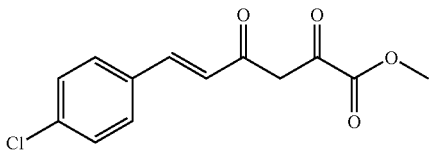

A solution of (E)-6-(4-chlorophenyl)-2,4-dioxo-hex-5-enoic acid ethyl ester (4; 33.39 g, 0.12 mol) and conc H$_2$SO$_4$ (0.5 mL) was stirred at reflux for 6 h in methyl alcohol (MeOH, 400 mL). Upon cooling and solvent concentration, (E)-6-(4-chlorophenyl)-2,4-dioxo-hex-5-enoic acid methyl ester (6; 22.7 g, 71%) was collected as yellow crystals: mp 135-136° C.; $^1$H NMR (400 MHz, CDCl$_3$) δ 14.74 (s, 1H), 7.67 (d, J=15.9 Hz, 1H), 7.49 (d, J=8.5 Hz, 2H), 7.38 (d, J=8.5 Hz, 2H), 6.61 (d, J=15.9 Hz, 1H), 6.53 (s, 1H), 3.92 (s, 3H); HRMS-ESI (m/z): calcd for C$_{13}$H$_{11}$ClO$_4$, 266.034. found, 266.034.

Example 4

Preparation of (2Z,5E)-2-amino-6-(4-chloro-2-fluorophenyl)-4-oxo-hexa-2,5-dienoic acid ethyl ester (7)

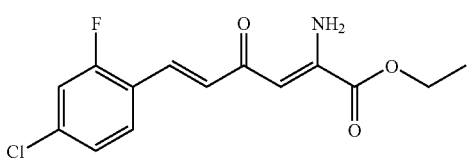

A mixture of (E)-6-(4-chloro-2-fluorophenyl)-2,4-dioxo-hex-5-enoic acid ethyl ester (3; 15.0 g, 0.05 mol) and ammonium acetate (7.7 g, 0.1 mol) in EtOH (100 mL) was stirred and heated to reflux for 1 h. The solvent was removed under reduced pressure, and the residue was dissolved in CH$_2$Cl$_2$ (200 mL) and washed with saturated aqueous sodium carbonate (Na$_2$CO$_3$, 100 mL). After drying over MgSO$_4$, silica gel (50 g) was added and the solvent was removed. The residue was washed with 20% ethyl acetate (EtOAc)/hexanes (300 mL) to give after solvent removal (2Z,5E)-2-amino-6-(4-chloro-2-fluorophenyl)-4-oxo-hexa-2,5-dienoic acid ethyl ester (7; 6.1 g, 41%) as a light orange solid: mp 102-103° C.; $^1$H NMR (400 MHz, CDCl$_3$) δ 9.4 (br s, 1H), 7.62 (d, J=15.9 Hz, 1H), 7.52 (t, J=8.5 Hz, 1H), 7.49 (d, J=8.3 Hz, 1H), 7.19-7.08 (m, 2H), 6.87 (d, J=15.9 Hz, 1H), 6.14 (s, 1H), 6.05 (br s, 1H), 4.37 (q, J=7.1 Hz, 2H), 1.39 (t, J=7.1 Hz, 3H); HRMS-ESI (m/z): calcd for C$_{14}$H$_{13}$ClFNO$_3$, 297.056. found, 297.056. Further washing of the silica gel with 40% EtOAc/hexanes (400 mL) gave more (2Z,5E)-2-amino-6-(4-chloro-2-fluorophenyl)-4-oxo-hexa-2,5-dienoic acid ethyl ester (7; 8.8 g of 70% pure by $^1$H NMR spectroscopy) for a total of 12.2 g (82%).

(2Z,5E)-2-Amino-6-(4-chlorophenyl)-4-oxo-hexa-2,5-dienoic acid ethyl ester (8)

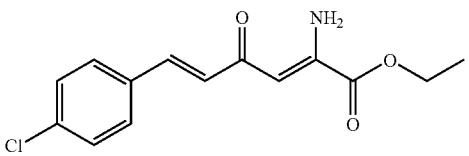

Using the procedure of Example 4, (E)-6-(4-chlorophenyl)-2,4-dioxo-hex-5-enoic acid ethyl ester (4; 79.5 g, 0.284 mol) and ammonium acetate (43.78 g, 0.568 mol) were allowed to react in EtOH (795 mL) to provide (2Z,5E)-2-amino-6-(4-chlorophenyl)-4-oxo-hexa-2,5-dienoic acid ethyl ester (8; 47 g, 86%) as a yellow solid: mp 105-107° C.; $^1$H NMR (400 MHz, CDCl$_3$) δ 9.40 (br s, 1H), 7.52 (d, J=15.9 Hz, 1H), 7.50-7.47 (m, 2H), 7.38-7.32 (m, 2H), 6.78 (d, J=15.9 Hz, 1H), 6.14 (s, 1H), 6.01 (s, 1H), 4.37 (q, J=7.1 Hz, 2H), 1.39 (t, J=7.1 Hz, 3H); HRMS-ESI (m/z): calcd for C$_{14}$H$_{14}$ClNO$_3$, 279.067. found, 279.066.

(2Z,5E)-2-Amino-6-(4-chlorophenyl)-4-oxo-hexa-2,5-dienoic acid methyl ester (9)

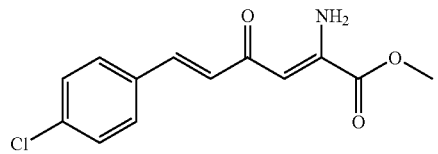

Using the procedure of Example 4, (E)-6-(4-chlorophenyl)-2,4-dioxo-hex-5-enoic acid methyl ester (6; 21.3 g, 0.008 mol) and ammonium acetate (12.33 g, 0.16 mol) were allowed to react in MeOH (150 mL) to afford (2Z,5E)-2-amino-6-(4-chlorophenyl)-4-oxo-hexa-2,5-dienoic acid methyl ester (9; 15.7 g, 74%) as a yellow solid: mp 112-113° C.; $^1$H NMR (400 MHz, CDCl$_3$) δ 9.37 (br s, 1H), 7.64-7.42 (m, 3H), 7.38-7.32 (m, 2H), 6.75 (d, J=15.9 Hz, 1H), 6.14 (s, 1H), 5.99 (br s, 1H), 3.91 (s, 3H); HRMS-ESI (m/z): calcd for $C_{13}H_{12}ClNO_3$, 265.050. found, 265.050.

2Z,5E)-2-Amino-6-(4-chloro-2-fluoro-3-methoxyphenyl)-4-oxo-hexa-2,5-dienoic acid ethyl ester (10)

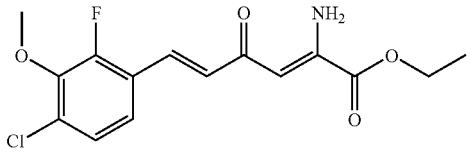

Using the procedure of Example 4, (E)-6-(4-chloro-2-fluoro-3-methoxyphenyl)-2,4-dioxo-hex-5-enoic acid ethyl ester (5; 37.8 g, 0.115 mol) and ammonium acetate (15.4 g, 0.2 mol) were allowed to react in EtOH (200 mL) to yield (2Z,5E)-2-amino-6-(4-chloro-2-fluoro-3-methoxyphenyl)-4-oxo-hexa-2,5-dienoic acid ethyl ester (10; 38.5 g, 92%, 90% pure by $^1$H NMR spectroscopy) as a dark orange solid. Treatment with silica gel (50 g) followed by eluting with 40% EtOAc/hexanes (400 mL) gave a yellow solid (25.3 g, 67%): mp 103-104° C.; $^1$H NMR (400 MHz, CDCl$_3$) δ 9.44 (br s, 1H), 7.63 (d, J=16.1 Hz, 1H), 7.23 (dd, J=8.6, 7.0 Hz, 1H), 7.16 (dd, J=8.6, 1.6 Hz, 1H), 6.87 (d, J=16.1 Hz, 1H), 6.15 (s, 1H), 6.04 (br s, 1H), 4.37 (q, J=7.1 Hz, 2H), 3.98 (d, J=1.2 Hz, 3H), 1.40 (t, J=7.1 Hz, 3H); HRMS-ESI (m/z): calcd for $C_{15}H_{15}ClFNO_4$, 327.067. found, 327.068.

Example 5

Preparation of 6-(4-chloro-2-fluorophenyl)-4-oxo-1,4,5,6-tetrahydropyridine-2-carboxylic acid ethyl ester (11)

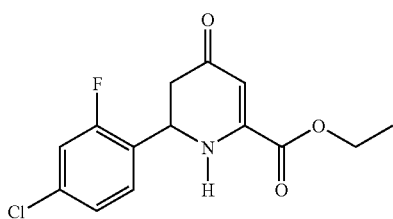

A solution of (2Z,5E)-2-amino-6-(4-chloro-2-fluorophenyl)-4-oxo-hexa-2,5-dienoic acid ethyl ester (7; 5.26 g, 0.0177 mol) in anhydrous 1,4-dioxane (100 mL) was heated to 185° C. in a 200 mL Parr reactor under a positive nitrogen (N$_2$) pressure. After 9 h, the reactor was cooled, and the solvent was removed under reduced pressure leaving a dark orange oil (5.85 g). By $^1$H NMR spectroscopy the material was 75% of the desired 6-(4-chloro-2-fluorophenyl)-4-oxo-1,4,5,6-tetrahydropyridine-2-carboxylic acid ethyl ester (11) along with 25% uncyclized 7. Purification on basic alumina eluting with 40% EtOAc/hexanes gave an off-white solid (1.4 g, 26%): mp 107-109° C.; $^1$H NMR (400 MHz, CDCl$_3$) δ 7.40 (t, J=8.1 Hz, 1H), 7.22-7.06 (m, 2H), 5.84 (s, 1H), 5.73 (s, 1H), 5.09 (t, J=8.9 Hz, 1H), 4.35 (q, J=7.1 Hz, 2H), 2.69 (d, J=8.9 Hz, 2H), 1.36 (t, J=7.1 Hz, 3H); HRMS-ESI (m/z): calcd for $C_{14}H_{13}ClFNO_3$, 297.057. found, 297.057.

Using the procedure of Example 5, (2Z,5E)-2-amino-6-(4-chloro-2-fluoro-phenyl)-4-oxo-hexa-2,5-dienoic acid ethyl ester (7; 88 g, 0.296 mol) in 1,4-dioxane (880 mL) in a 2 liter Parr reactor gave, following purification by silica gel chromatography eluting with 40% EtOAc/hexanes, 6-(4-chloro-2-fluorophenyl)-4-oxo-1,4,5,6-tetrahydropyridine-2-carboxylic acid ethyl ester (11; 43 g, 49%, 96% pure by HPLC) as a tan solid.

6-(4-Chlorophenyl)-4-oxo-1,4,5,6-tetrahydropyridine-2-carboxylic acid ethyl ester (12)

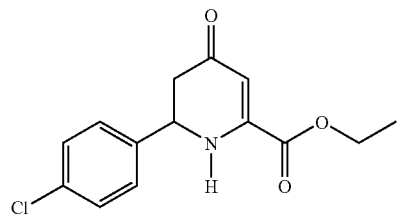

Using the procedure of Example 5, (2Z,5E)-2-amino-6-(4-chlorophenyl)-4-oxo-hexa-2,5-dienoic acid ethyl ester (8; 47 g, 0.168 mol) in 1,4-dioxane (470 mL) in a 2 liter Parr reactor gave, following purification by silica gel chromatography eluting with 40% EtOAc/hexanes, 6-(4-chlorophenyl)-4-oxo-1,4,5,6-tetrahydropyridine-2-carboxylic acid ethyl ester (12; 25 g, 49%, 99% pure by HPLC) as an off-white solid: mp 93-94° C.; $^1$H NMR (400 MHz, CDCl$_3$) δ 7.36 (q, J=8.6 Hz, 4H), 5.82 (s, 1H), 5.72 (br s, 1H), 4.74 (dd, J=14.2, 5.0 Hz, 1H), 4.35 (q, J=7.1 Hz, 2H), 2.68 (dd, J=16.3, 14.2 Hz, 1H), 2.58 (dd, J=16.4, 5.0 Hz, 1H), 1.36 (t, J=7.1 Hz, 3H); HRMS-ESI (m/z): calcd for $C_{14}H_{14}ClNO_3$, 279.067. found, 279.066.

6-(4-Chlorophenyl)-4-oxo-1,4,5,6-tetrahydropyridine-2-carboxylic acid methyl ester (13)

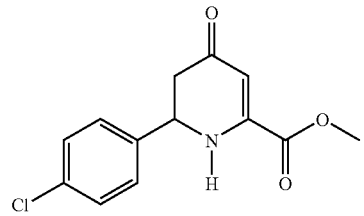

Using the procedure of Example 5, (2Z,5E)-2-amino-6-(4-chlorophenyl)-4-oxo-hexa-2,5-dienoic acid methyl ester (9; 6.64 g, 0.025 mol) in 1,4-dioxane (100 mL) in a 200 mL Parr reactor gave, after trituration with ether/pentane, 6-(4-chlorophenyl)-4-oxo-1,4,5,6-tetrahydropyridine-2-carboxylic acid methyl ester (13; 6.12 g, 91%, 98% pure by GC) as an off-white solid: mp 113-114° C.; $^1$H NMR (400 MHz, CDCl$_3$) δ 7.36 (q, J=8.6 Hz, 4H), 5.82 (s, 1H), 5.72 (br s, 1H), 4.74 (dd, J=14.2, 5.0 Hz, 1H), 4.74 (dd, J=14.2, 5.0 Hz, 1H), 3.90 (s, 3H), 2.68 (dd, J=16.3, 14.2 Hz, 1H), 2.58 (dd, J=16.4, 5.0 Hz, 1H); HRMS-ESI (m/z): calcd for $C_{13}H_{12}ClNO_3$, 265.050. found, 265.051.

6-(4-Chloro-2-fluoro-3-methoxyphenyl)-4-oxo-1,4,5,6-tetrahydropyridine-2-carboxylic acid ethyl ester (14)

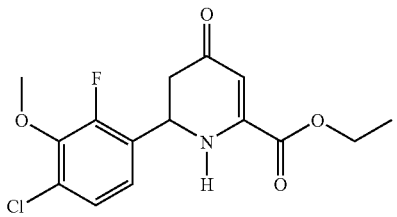

Using the procedure of Example 5, (2Z,5E)-2-amino-6-(4-chloro-2-fluoro-3-methoxyphenyl)-4-oxo-hexa-2,5-dienoic acid ethyl ester (10; 6.55 g, 0.02 mol) in 1,4-dioxane (100 mL) in a 200 mL Parr reactor gave, after trituration with ether/pentane, 6-(4-chloro-2-fluoro-3-methoxyphenyl)-4-oxo-1,4,5,6-tetrahydropyridine-2-carboxylic acid ethyl ester (14; 5.9 g, 90%, 98% pure by GC) as an off-white solid: mp 116-118° C.; $^1$H NMR (400 MHz, CDCl$_3$) δ 7.22 (dd, J=8.5, 1.8 Hz, 1H), 7.09 (dd, J=8.4, 7.1 Hz, 1H), 5.93 (s, 1H), 5.90 (s, 1H), 5.21-5.08 (m, 1H), 4.37 (q, J=7.1 Hz, 2H), 3.99 (d, J=1.3 Hz, 3H), 2.87-2.73 (m, 2H), 1.38 (t, J=7.1 Hz, 3H); HRMS-ESI (m/z): calcd for C$_{15}$H$_{15}$ClFNO$_4$, 327.067. found, 327.067.

Example 6

Preparation of 6-(4-chloro-2-fluoro-3-methoxyphenyl)-4-oxo-5,6-dihydro-4H-pyridine-1,2-dicarboxylic acid 2-methyl ester 1-phenyl ester (15)

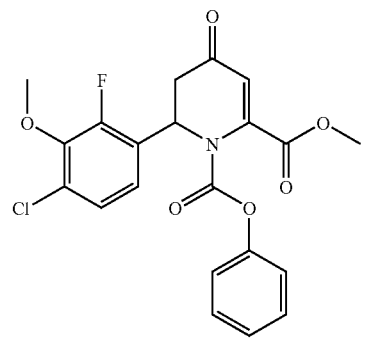

2-Chloro-6-fluoroanisole (24.5 g, 0.153 mol) was dissolved in anhydrous THF (150 mL) under a nitrogen atmosphere. The solution was cooled to −60° C., and n-BuLi (67 mL of 2.5 M solution in hexane, 0.168 mol) was added dropwise over 30 min. During the addition the reaction warmed to −48° C. The reaction mixture was stirred for 30 min at −50° C. and then cooled to −60° C. Anhydrous ZnCl$_2$ (25 g, 0.183 mol) was added to the reaction mixture first by addition as a solid and then by addition of a solution in anhydrous THF. The reaction mixture was stirred at −45° C. for 2.5 h until nearly all of the solid ZnCl$_2$ had dissolved. The reaction solution was allowed to warm to room temperature, and solvent was evaporated by a nitrogen purge. The residue was redissolved in THF to form a stock solution.

Methyl 4-methoxypicolinate (11.92 g, 0.0713 mol) was dissolved in anhydrous THF (300 mL) under N$_2$. The solution was cooled in an ice bath. Neat phenyl chloroformate (10.5 mL, 0.0837 mol) was added. After 45 min the stock solution of (4-chloro-2-fluoro-3-methoxyphenyl)zinc(II) chloride (1.19 M in THF, 76.0 mL, 0.0904 mol) was added dropwise over 1 h. The solution was stirred at room temperature for 3 days (d) and then quenched by addition of a saturated aqueous ammonium chloride (NH$_4$Cl) solution (200 mL). The organic layer was separated, and the aqueous layer was extracted with ether (2×100 mL). The combined organic extracts were washed with H$_2$O and then brine. The solution was dried (MgSO$_4$) and evaporated to a bright yellow liquid which was dissolved in THF (250 mL) and 1 M HCl (250 mL). The reaction mixture was stirred at room temperature for 2 d and then neutralized with saturated NaHCO$_3$ solution. The reaction mixture was extracted with ether. The ether extracts were washed with H$_2$O followed by brine, then dried (MgSO$_4$) and evaporated to a yellow oil. The crude product was purified by silica gel chromatography (hexane-EtOAc gradient) to give a yellow oil. The oil was crystallized from MeOH to give 6-(4-chloro-2-fluoro-3-methoxyphenyl)-4-oxo-5,6-dihydro-4H-pyridine-1,2-dicarboxylic acid 2-methyl ester 1-phenyl ester (15; 17.67 g, 57%) as a white solid: mp 112-114° C.; $^1$H NMR (300 MHz, CDCl$_3$) δ 7.40 (m, 2H), 7.27 (m, 1H), 7.14 (m, 4H), 6.22 (d, J=6.6 Hz, 1H, H6), 5.90 (d, J=1.2 Hz, 1H, H3), 3.97 (d, $J_{F-H}$=0.9 Hz, 3H, OMe), 3.87 (s, 3H, CO$_2$Me), 3.30 (dd, J=6.6, 17.4 Hz, 1H, H5a), 3.05 (d, J=18 Hz, 1H, H5b); $^{13}$C{$^1$H} NMR (75.4 MHz, CDCl$_3$) δ 191.7 (C4), 163.8 (CO$_2$Me), 153.9 (d, $J_{F-C}$=250 Hz, C2'), 151.0, 150.3, 145.0, 144.8, 129.6 (meta Ph), 128.8 (d, $J_{F-C}$=3 Hz, C4'), 126.5 (para Ph), 125.2 (d, $J_{F-C}$=3 Hz, C5'), 124.5 (d, $J_{F-C}$=12 Hz, C1'), 121.0 (d, $J_{F-C}$=4 Hz, C6'), 120.9 (ortho Ph), 114.5 (C3), 61.6 (d, $J_{F-C}$=5 Hz, OMe), 53.8, 53.4, 41.6; Anal. Calcd for C$_{21}$H$_{17}$ClFNO$_6$: C, 58.14; H, 3.95; N, 3.23. Found: C, 57.82; H, 3.90; N, 3.18.

Example 7

Preparation of 6-(4-chloro-2-fluoro-3-methoxyphenyl)-4-oxo-1,4,5,6-tetrahydropyridine-2-carboxylic acid methyl ester (16)

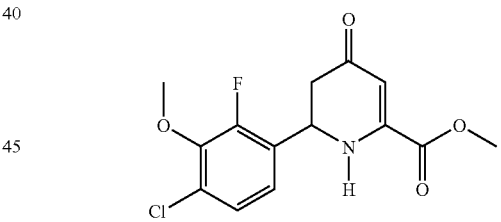

6-(4-Chloro-2-fluoro-3-methoxyphenyl)-4-oxo-5,6-dihydro-4H-pyridine-1,2-dicarboxylic acid 2-methyl ester 1-phenyl ester (15; 7.213 g, 0.0166 mol) was slurried in MeOH (80 mL). The suspension was cooled in an ice bath, and solid sodium methoxide (NaOMe; 1.08 g, 0.02 mol) was added. After 1 h, the reaction was quenched with saturated aqueous NH$_4$Cl solution (80 mL) and H$_2$O (50 mL) and then cooled in ice. The precipitate was filtered, washed with H$_2$O followed by cold MeOH and dried in air to give 6-(4-chloro-2-fluoro-3-methoxyphenyl)-4-oxo-1,4,5,6-tetrahydropyridine-2-carboxylic acid methyl ester (16; 4.93 g, 94%) as a white powder: mp 164.9-166.2° C.; $^1$H NMR (300 MHz, CDCl$_3$) δ 7.20 (dd, $J_{F-H}$=1.8 Hz, $J_{H-H}$=8.7 Hz, 1H, aromatic), 7.10 (dd, $J_{F-H}$=6.9 Hz, $J_{H-H}$=8.7 Hz, 1H, aromatic), 5.84 (d, J=0.9 Hz, 1H, H3), 5.68 (br s, 1H, NH), 5.10 (t, J=9.3 Hz, 1H, H6), 3.98 (d, $J_{F-H}$=1.5 Hz, 3H, OMe), 3.91 (s, 3H, CO$_2$Me), 2.71 (d, J=9 Hz, 2H, H5); $^{13}$C{$^1$H} NMR (75.4 MHz, CDCl$_3$) δ 193.0 (C4), 163.6 (CO$_2$Me), 153.8 (d, $J_{F-C}$=251 Hz, C2'), 147.9 (C2), 144.6 (d, $J_{F-C}$=13 Hz, C3'), 128.6 (d, $J_{F-C}$=3 Hz, C1'/

C4'), 126.8 (d, $J_{F-C}$=11 Hz, C1'/C4'), 125.5 (d, $J_{F-C}$=3 Hz, C5'), 121.5 (d, $J_{F-C}$=4 Hz, C6'), 102.0 (C3), 61.6 (d, $J_{F-C}$=5 Hz, OMe), 53.4, 50.8, 42.0; HRMS-ESI (m/z): calcd for $C_{14}H_{13}ClFNO_4$, 313.0512. found, 313.0511; Anal. Calcd for $C_{14}H_{13}ClFNO_4$: C, 53.60; H, 4.18; N, 4.46. Found: C, 53.30; H, 4.14; N, 4.35.

Example 8

Preparation of 6-(4-chloro-2-fluorophenyl)-4-hydroxyimino-1,4,5,6-tetrahydropyridine-2-carboxylic acid ethyl ester (17)

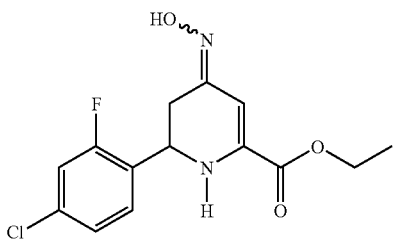

A mixture of 6-(4-chloro-2-fluorophenyl)-4-oxo-1,4,5,6-tetrahydropyridine-2-carboxylic acid ethyl ester (11, 41 g, 0.138 mol), hydroxylamine hydrochloride (38.3 g, 0.552 mol), and pyridine (82 mL) in EtOH (400 mL) was heated to reflux for 1 h. The reaction mixture was cooled to room temperature and the solvent was removed. The residue was triturated with ice-cold $H_2O$ to give a 3:2 mixture of syn and anti isomers of 6-(4-chloro-2-fluorophenyl)-4-hydroxyimino-1,4,5,6-tetrahydropyridine-2-carboxylic acid ethyl ester (17; 24 g, 56%, 98% pure by HPLC) as a tan solid: mp 124-126° C.; $^1$H NMR (400 MHz, DMSO-$d_6$) major isomer δ 9.3 (br s, 1H), 7.40 (m, 1H), 7.27 (m, 2H), 6.76 (br s, 1H), 6.21 (s, 1H), 4.80 (br s, 1H), 4.42-4.13 (m, 2H), 2.69 (dd, J=14.9, 4.9 Hz, 1H), 2.62-2.45 (m, 1H), 1.30 (t, J=6.8 Hz, 3H); $^1$H NMR (400 MHz, DMSO-$d_6$) minor isomer δ 9.3 (br s, 1H), 7.40 (m, 1H), 7.27 (m, 2H), 6.12 (br s, 1H), 5.95 (s, 1H), 4.64 (dd, J=8.4, 5.1 Hz, 1H), 4.42-4.13 (m, 2H), 2.91 (dd, J=16.5, 4.9 Hz, 1H), 2.52 (m, 1H), 1.27 (t, J=6.5 Hz, 3H); HRMS-ESI (m/z): calcd for $C_{14}H_{14}ClFN_2O_3$, 312.068. found, 312.067.

6-(4-Chloro-2-fluoro-3-methoxyphenyl)-4-hydroxyimino-1,4,5,6-tetrahydropyridine-2-carboxylic acid methyl ester (18)

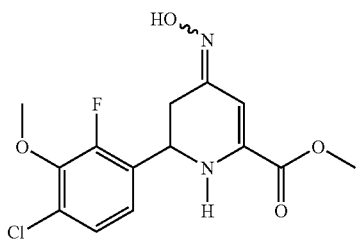

6-(4-Chloro-2-fluoro-3-methoxyphenyl)-4-oxo-1,4,5,6-tetrahydropyridine-2-carboxylic acid methyl ester (16, 5.19 g, 16.5 mmol) was slurried in methanol (160 mL). Hydroxylamine hydrochloride (3.35 g, 48.3 mmol) was added, followed by pyridine (10.0 mL, 123 mmol). The reaction mixture was stirred at reflux for 120 min. Methanol was evaporated under vacuum. $H_2O$ (200 mL) was added, and the residue was extracted into ether (4×150 mL). The combined extracts were washed with brine, dried (MgSO$_4$) and evaporated under vacuum to give 6-(4-chloro-2-fluoro-3-methoxyphenyl)-4-hydroxyimino-1,4,5,6-tetrahydropyridine-2-carboxylic acid methyl ester (18; 4.54 g, 80%) as a white solid: mp 136-138° C. A 1:1 mixture of syn and anti isomers was observed by NMR spectroscopy and HPLC. $^1$H NMR (400 MHz, $C_6D_6$) δ 8.34 (br, 1H, NOH), 8.25 (br, 1H, NOH), 7.00 (s, 1H, H3), 6.71 (dd, $J_{F-H}$=1.5 Hz, $J_{H-H}$=9 Hz, 1H, aromatic), 6.69 (dd, $J_{F-H}$=1.8 Hz, $J_{H-H}$=9 Hz, 1H, aromatic), 6.57 (dd, $J_{F-H}$=$J_{H-H}$=7.5 Hz, 1H, aromatic), 6.53 (s, 1H, H3), 6.50 (dd, $J_{F-H}$=$J_{H-H}$=7.5 Hz, 1H, aromatic), 4.72 (s, 1H, NH), 4.52 (s, 1H, NH), 4.38 (dd, $J_{H-H}$=3.6, 10.2 Hz, 1H, H6, isomer A), 4.23 (dd, $J_{H-H}$=3.9, 11.4 Hz, 1H, H6, isomer B), 3.53 (s, 6H, CO$_2$Me), 3.24 (s, 3H, OMe), 3.23 (s, 3H, OMe), 3.30 (dd, $J_{H-H}$=4.2, 16.8 Hz, 1H, H5, isomer B), 2.63 (dd, $J_{H-H}$=4.2, 15.3 Hz, 1H, H5, isomer A), 2.44 (dd, $J_{H-H}$=10.5, 15.3 Hz, 1H, H5, isomer A), 2.33 (dd, $J_{H-H}$=11.1, 16.8 Hz, 1H, H5, isomer B); $^{13}$C{$^1$H} NMR (CDCl$_3$) δ 164.2 (CO$_2$Me), 163.9 (CO$_2$Me), 153.7 (d, $J_{F-C}$=250 Hz, C2'), 153.6 (d, $J_{F-C}$=251 Hz, C2'), 152.6 (C4), 149.6 (C4), 144.3 (d, $J_{F-C}$=3 Hz, C3'), 144.1 (d, $J_{F-C}$=3 Hz, C3'), 139.2, 138.3, 128.6 (d, $J_{F-C}$=12 Hz), 127.9 (d, $J_{F-C}$=11 Hz), 127.8 (d, $J_{F-C}$=3 Hz), 127.7 (d, $J_{F-C}$=3 Hz), 125.3, 121.7, 101.7 (C3), 92.6 (C3), 61.42, 61.38, 52.7, 52.6, 49.3, 48.3, 33.6 (C5), 28.7 (C5). HRMS-ESI (m/z) calcd for $C_{14}H_{14}ClFN_2O_4$, 328.0621. found, 328.0620. Anal. Calcd for $C_{14}H_{14}ClFN_2O_4$: C, 51.15; H, 4.29; N, 8.52. Found: C, 51.31; H, 4.34; N, 8.40.

Example 9

Preparation of 6-(4-chlorophenyl)-4-hydroxyimino-1,4,5,6-tetrahydropyridine-2-carboxylic acid ethyl ester (19)

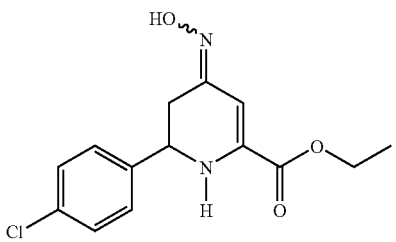

A mixture of 6-(4-chlorophenyl)-4-oxo-1,4,5,6-tetrahydropyridine-2-carboxylic acid ethyl ester (12; 5.6 g, 0.02 mol) and 50% aqueous hydroxylamine (3 mL, 0.045 mol) in toluene (100 mL) was stirred at reflux for 2 h. After solvent removal the residue was added to $CH_2Cl_2$ (100 mL), washed with a saturated aqueous solution of NaCl, dried (MgSO$_4$), and the solvent was removed to give an orange solid (5.8 g). Trituration with ether/pentane gave a 3:2 mixture of syn and anti isomers of 6-(4-chlorophenyl)-4-hydroxyimino-1,4,5,6-tetrahydropyridine-2-carboxylic acid ethyl ester (19; 4.85 g, 85%) as an off-white solid: mp 159-160° C.; $^1$H NMR (400 MHz, CDCl$_3$) major isomer δ 9.3 (br, 1H), 7.35-7.25 (m, 4H), 6.19 (s, 1H), 4.88 (s, 1H), 4.36-4.25 (m, 3H), 3.35-3.23 (m, 1H), 2.35 (dd, J=16.8, 12.8 Hz, 1H), 1.34 (t, J=7.1 Hz, 3H); $^1$H NMR (400 MHz, CDCl$_3$) minor isomer δ 9.3 (br s, 1H), 7.35-7.25 (m, 4H), 6.57 (s, 1H), 5.19 (s, 1H), 4.57-4.38 (m, 1H), 4.36-4.25 (m, 2H), 2.72-2.54 (m, 2H), 1.34-1.31 (m, 3H); HRMS-ESI (m/z): calcd for $C_{14}H_{15}ClN_2O_3$, 294.077. found, 294.077.

Example 10

Preparation of 6-(4-chloro-2-fluorophenyl)-4-[(E,Z)-methanesulfonyloximino]-1,4,5,6-tetrahydropyridine-2-carboxylic acid ethyl ester (20)

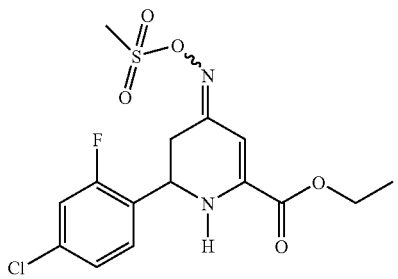

To a magnetically-stirred solution of 6-(4-chloro-2-fluorophenyl)-4-hydroxyimino-1,4,5,6-tetrahydropyridine-2-carboxylic acid ethyl ester (17; 22.0 g, 0.0705 mol) in $CH_2Cl_2$ (220 mL) was added triethylamine (19.6 mL, 0.141 mol). The reaction mixture was cooled in an ice bath and methanesulfonyl chloride (8.8 mL, 0.113 mol) was added dropwise over 30 min. Upon warming to room temperature overnight, the reaction mixture was diluted with $CH_2Cl_2$ (200 mL), washed with saturated aqueous solutions of $NaHCO_3$ and NaCl, and dried ($Na_2SO_4$). Solvent removal followed by trituration with ether/pentane gave an 8:1 mixture of isomers of 6-(4-chloro-2-fluorophenyl)-4-[(E,Z)-methanesulfonyl-oximino]-1,4,5,6-tetrahydropyridine-2-carboxylic acid ethyl ester (20; 10.5 g, 39%, 95% pure by $^1$H NMR) as an off-white solid: mp 114-116° C.; $^1$H NMR (400 MHz, $CDCl_3$) major isomer δ 7.36 (t, J=8.1 Hz, 1H), 7.19 (dd, J=8.3, 1.6 Hz, 1H), 7.15 (dd, J=10.1, 1.9 Hz, 1H), 6.37 (s, 1H), 5.59 (s, 1H), 4.93 (dd, J=10.9, 4.4 Hz, 1H), 4.35 (q, J=7.1 Hz, 2H), 3.15 (s, 3H), 2.92-2.68 (m, 2H), 1.38 (t, J=7.1 Hz, 3H); HRMS-ESI (m/z): calcd for $C_{15}H_{16}ClFN_2O_5S$, 390.0447. found, 390.0444.

6-(4-Chlorophenyl)-4-[(E,Z)-methanesulfonyloximino]-1,4,5,6-tetrahydropyridine-2-carboxylic acid methyl ester (21)

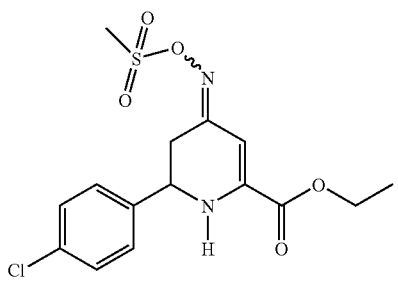

Using the procedure of Example 10, 6-(4-chlorophenyl)-4-hydroxyimino-1,4,5,6-tetrahydropyridine-2-carboxylic acid ethyl ester (19; 13.0 g, 0.0442 mol), methanesulfonyl chloride (5.5 mL, 0.0707 mol), and triethylamine (12.3 mL, 0.0884 mol) gave an 8:1 mixture of isomers of 6-(4-chlorophenyl)-4-[(E,Z)-methanesulfonyloximino]-1,4,5,6-tetrahydropyridine-2-carboxylic acid ethyl ester (21; 10.5 g, 86%, 97% pure by HPLC) as an off-white solid: mp 113-115° C.; $^1$H NMR (400 MHz, $CDCl_3$) major isomer δ 7.45-7.29 (m, 4H), 6.36 (s, 1H), 5.59 (s, 1H), 4.56 (dd, J=11.7, 5.3 Hz, 1H), 4.35 (q, J=7.1, 1.3 Hz, 2H), 3.15 (s, 3H), 2.82-2.67 (m, 2H), 1.38 (t, J=7.1 Hz, 3H); HRMS-ESI (m/z): calcd for $C_{15}H_{17}ClN_2O_5S$, 372.055. found, 372.055.

Example 11

Preparation of 6-(4-chloro-2-fluoro-3-methoxyphenyl)-4-[(E,Z)-p-toluenesulfonyloximino]-1,4,5,6-tetrahydropyridine-2-carboxylic acid methyl ester (22)

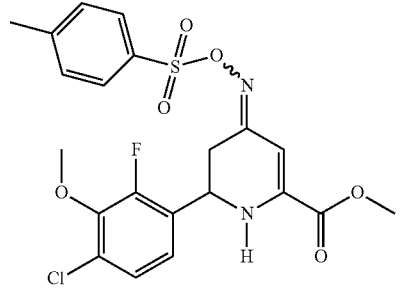

To a magnetically-stirred solution of 6-(4-chloro-2-fluoro-3-methoxyphenyl)-4-hydroxyimino-1,4,5,6-tetrahydropyridine-2-carboxylic acid methyl ester (18; 0.657 g, 0.002 mol) in pyridine (5 mL) cooled in an ice bath was added p-toluenesulfonyl chloride (0.572 g, 0.003 mol) over 5 min. After allowing the reaction mixture to warm to room temperature for 2 d, the solvent was removed under reduced pressure. The residue was dissolved in $CH_2Cl_2$ (50 mL), washed with saturated aqueous solutions of $NaHCO_3$ and NaCl, and dried ($MgSO_4$). Solvent removal gave a viscous orange oil (1.12 g). Trituration with ether/pentane gave a 4:1 mixture of isomers of 6-(4-chloro-2-fluoro-3-methoxyphenyl)-4-[(E,Z)-p-toluenesulfonyloximino]-1,4,5,6-tetrahydropyridine-2-carboxylic acid methyl ester (22; 0.818 g, 85%) as an off-white solid: mp 147-148° C.; $^1$H NMR (400 MHz, $CDCl_3$) δ 7.85 (d, J=8.3 Hz, 2H), 7.32 (d, J=8.0 Hz, 2H), 7.11 (dd, J=8.5, 1.7 Hz, 1H), 6.95 (dd, J=8.3, 7.2 Hz, 1H), 6.39 (s, 1H), 5.47 (s, 1H), 4.84 (dd, J=10.6, 4.5 Hz, 1H), 3.95 (d, J=1.1 Hz, 3H), 3.89 (s, 3H), 2.71 (ddd, J=26.3, 15.5, 7.7 Hz, 2H), 2.45 (s, 3H); HRMS-ESI (m/z): calcd for $C_{21}H_{20}ClFN_2O_6S$, 482.0709. found, 482.0701.

Example 12

Preparation of 6-(4-chloro-2-fluoro-3-methoxyphenyl)-4-[(E,Z)-methanesulfonyloximino]-1,4,5,6-tetrahydropyridine-2-carboxylic acid methyl ester (23)

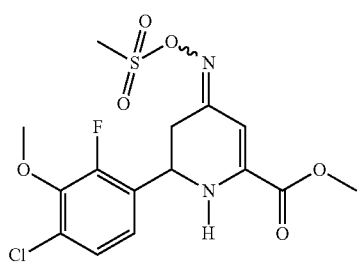

Step A: To a magnetically-stirred solution of 6-(4-chloro-2-fluoro-3-methoxyphenyl)-4-oxo-1,4,5,6-tetrahydropyridine-2-carboxylic acid methyl ester (16; 4.70 g, 0.015 mol) in MeOH (100 mL) at room temperature was added hydroxylamine hydrochloride (2.08 g, 0.03 mol), followed by pyridine (8 mL). After refluxing the mixture for 1 h, the solvent was removed under reduced pressure. The residue was dissolved in $CH_2Cl_2$ (100 mL) and was washed with saturated aqueous solutions of $NaHCO_3$ and NaCl. After drying ($MgSO_4$), solvent removal gave a 1:1 mixture of isomers of 6-(4-chloro-2-fluorophenyl-3-methoxyphenyl)-4-hydroxyimino-1,4,5,6-tetrahydropyridine-2-carboxylic acid methyl ester (18; 4.95 g, 100% crude yield) as a yellow solid.

Step B: To a magnetically-stirred solution of 6-(4-chloro-2-fluoro-3-methoxyphenyl)-4-hydroxyimino-1,4,5,6-tetrahydropyridine-2-carboxylic acid methyl ester (18; 4.95 g, 0.015 mol) in pyridine (30 mL) cooled in an ice bath was added methanesulfonyl chloride (3.43 g, 0.03 mol) over 5 min. After allowing the reaction mixture to warm to room temperature for 2 d, solvent was removed under reduced pressure. The residue was dissolved in $CH_2Cl_2$ (100 mL), washed with saturated aqueous solutions of $NaHCO_3$ and NaCl, and dried ($MgSO_4$). Solvent removal gave a tacky light orange solid (5.5 g). Trituration with ether/pentane gave an 8:1 mixture of isomers of 6-(4-chloro-2-fluoro-3-methoxyphenyl)-4-[(E,Z)-methanesulfonyloximino]-1,4,5,6-tetrahydropyridine-2-carboxylic acid methyl ester (23; 4.14 g, 68%) as a white solid: mp 134-135° C.; $^1$H NMR (400 MHz, $CDCl_3$) major isomer δ 7.20 (dd, J=8.8, 1.3 Hz, 1H), 7.06 (dd, J=8.5, 6.7 Hz, 1H), 6.4 (s, 1H), 5.59 (br s, 1H), 4.93 (dd, J=10.8, 4.7 Hz, 1H), 3.96 (s, 3H), 3.90 (s, 3H), 3.15 (s, 3H), 2.81 (m, 2H); HRMS-ESI (m/z): calcd for $C_{15}H_{16}ClFN_2O_6S$, 406.040. found, 406.040.

6-(4-Chlorophenyl)-4-[(E,Z)-methanesulfonyloximino]-1,4,5,6-tetrahydropyridine-2-carboxylic acid methyl ester (24)

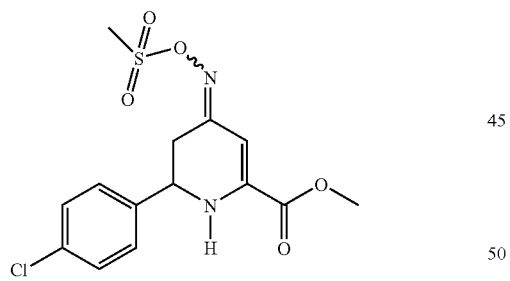

Using the procedure of Example 12, 6-(4-chlorophenyl)-4-oxo-1,4,5,6-tetrahydropyridine-2-carboxylic acid methyl ester (13; 6.64 g, 0.025 mol), hydroxylamine hydrochloride (3.47 g, 0.05 mol), and pyridine (10 mL) gave an orange oil (9.1 g) after work-up. This material was redissolved in pyridine (40 mL) and treated with methanesulfonyl chloride (5.72 g, 0.05 mol) to provide a 4:1 mixture of isomers of 6-(4-chlorophenyl)-4-[(E,Z)-methanesulfonyloximino]-1,4,5,6-tetrahydropyridine-2-carboxylic acid methyl ester (24; 3.5 g, 39%, 95% pure by $^1$H NMR) as an off-white solid: mp 62-64° C.; $^1$H NMR (400 MHz, $CDCl_3$) major isomer δ 7.42-7.28 (m, 4H), 6.39 (s, 1H), 5.55 (s, 1H), 4.57 (dd, J=11.6, 5.1 Hz, 1H), 3.90 (s, 3H), 3.14 (s, 3H), 2.93-2.65 (m, 2H); minor isomer δ 7.45-7.28 (m, 4H), 6.15 (s, 1H), 5.23 (s, 1H), 4.41 (dd, J=13.4, 4.3 Hz, 1H), 3.90 (s, 3H), 3.30 (dd, J=17.2, 4.3 Hz, 1H), 3.15 (s, 3H), 2.56 (dd, J=17.1, 13.5 Hz, 1H); HRMS-ESI (m/z): calcd for $C_{14}H_{15}ClN_2O_5S$, 358.0384. found, 358.0385.

6-(4-Chloro-2-fluoro-3-methoxyphenyl)-4-[(E,Z)-methanesulfonyloximino]-1,4,5,6-tetrahydropyridine-2-carboxylic acid ethyl ester (25)

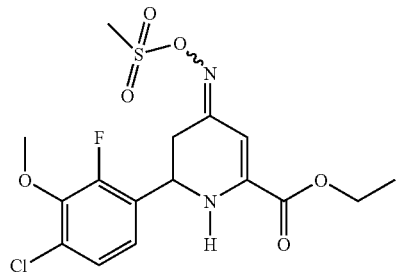

Using the procedure of Example 12, 6-(4-chloro-2-fluoro-3-methoxyphenyl)-4-oxo-1,4,5,6-tetrahydropyridine-2-carboxylic acid ethyl ester (14; 3.93 g, 0.012 mol), hydroxylamine hydrochloride (2.08 g, 0.03 mol), and pyridine (8 mL) gave a tacky orange solid (5.1 g) after work-up. This material was redissolved in pyridine (30 mL) and treated with methanesulfonyl chloride (2.75 g, 0.024 mol) to afford a 4:1 mixture of isomers of 6-(4-chloro-2-fluoro-3-methoxyphenyl)-4-[(E,Z)-methanesulfonyloximino]-1,4,5,6-tetrahydropyridine-2-carboxylic acid ethyl ester (25; 2.6 g, 52%, 95% pure by $^1$H NMR) as a white solid: mp 130-132° C.; $^1$H NMR (400 MHz, $CDCl_3$) δ 7.20 (dd, J=8.5, 1.5 Hz, 1H), 7.10-7.05 (m, 1H), 6.37 (s, 1H), 5.60 (s, 1H), 4.93 (dd, J=11.1, 4.4 Hz, 1H), 4.45-4.34 (m, 2H), 3.98 (d, J=1.1 Hz, 3H), 3.16 (s, 3H), 2.95-2.74 (m, 2H), 1.40 (d, J=7.1 Hz, 3H); HRMS-ESI (m/z): calcd for $C_{16}H_{18}ClFN_2O_6S$, 420.056. found, 420.056.

Example 13

Preparation of 3-chloro-6-(4-chloro-2-fluorophenyl)-4-[(E)-methanesulfonyloximino]-1,4,5,6-tetrahydropyridine-2-carboxylic acid methyl ester (26)

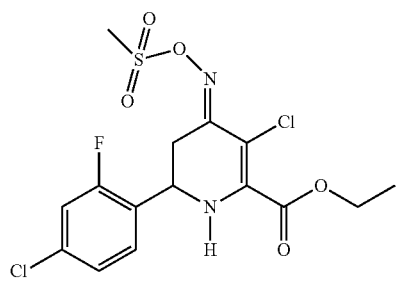

To a magnetically-stirred solution of 6-(4-chloro-2-fluorophenyl)-4-[(E,Z)-methanesulfonyloximino]-1,4,5,6-tetrahydropyridine-2-carboxylic acid ethyl ester (20; 2.74 g, 0.007 mol) in $CH_2Cl_2$ (20 mL) cooled with an ice bath was added a solution of sulfuryl chloride ($SO_2Cl_2$, 0.94 g, 0.007 mol) in $CH_2Cl_2$ over 5 min. After allowing the reaction mixture to warm to room temperature for 1 h, $CH_2Cl_2$ (50 mL)

was added. After washing the reaction mixture with a saturated aqueous solution of NaCl and drying (MgSO$_4$), solvent removal gave 3-chloro-6-(4-chloro-2-fluoro-phenyl)-4-[(E)-methanesulfonyloximino]-1,4,5,6-tetrahydropyridine-2-carboxylic acid ethyl ester (26; 2.91 g, 98%, 95% pure by $^1$H NMR) as a fluffy light yellow solid: mp 63-64° C.; $^1$H NMR (400 MHz, CDCl$_3$) δ 7.37 (t, J=8.1 Hz, 1H), 7.20 (dd, J=8.4, 1.7 Hz, 1H), 7.16 (dd, J=10.1, 2.0 Hz, 1H), 5.31 (s, 1H), 4.78 (dd, J=12.6, 4.5 Hz, 1H), 4.41 (q, J=7.1 Hz, 2H), 3.39 (dd, J=16.9, 4.4 Hz, 1H), 3.22 (s, 3H), 2.91-2.76 (m, 1H), 1.40 (t, J=7.1 Hz, 3H); HRMS-ESI (m/z): calcd for C$_{15}$H$_{15}$Cl$_2$FN$_2$O$_5$S, 425.240. found, 425.240.

3-Chloro-6-(4-chlorophenyl)-4-[(E)-methanesulfonyloximino]-1,4,5,6-tetrahydropyridine-2-carboxylic acid methyl ester (27)

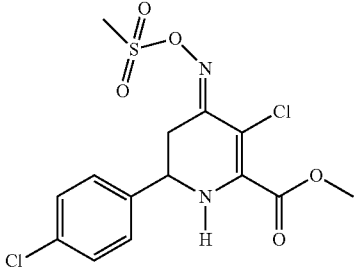

Using the procedure of Example 13, 6-(4-chlorophenyl)-4-[(E,Z)-methanesulfonyloximino]-1,4,5,6-tetrahydropyridine-2-carboxylic acid methyl ester (24; 2.78 g, 0.008 mol) and SO$_2$Cl$_2$ (1.08 g, 0.005 mol) in CH$_2$Cl$_2$ (25 mL) gave 3-chloro-6-(4-chlorophenyl)-4-[(E)-methanesulfonyloximino]-3-chloro-1,4,5,6-tetrahydropyridine-2-carboxylic acid methyl ester (27; 3.20 g, 99%, 95% pure by $^1$H NMR) as a fluffy light yellow solid: mp 60-62° C.; $^1$H NMR (400 MHz, CDCl$_3$) δ 7.41-7.29 (m, 4H), 5.33 (s, 1H), 4.44 (dd, J=13.8, 4.1 Hz, 1H), 3.94 (s, 3H), 3.40 (ddd, J=16.9, 4.2, 1.8 Hz, 1H), 3.21 (s, 3H), 2.88-2.57 (m, 1H); HRMS-ESI (m/z): calcd for C$_{15}$H$_{14}$Cl$_2$N$_2$O$_5$S, 391.9995. found, 391.9997.

3-Chloro-6-(4-chlorophenyl)-4-[(E)-methanesulfonyloximino]-1,4,5,6-tetrahydropyridine-2-carboxylic acid ethyl ester (28)

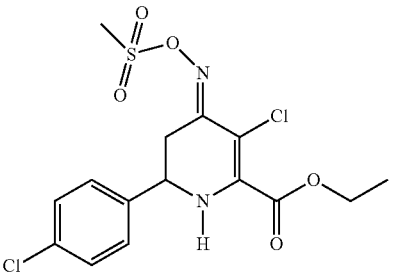

Using the procedure of Example 13, 6-(4-chlorophenyl)-4-[(E,Z)-methanesulfonyloximino]-1,4,5,6-tetrahydropyridine-2-carboxylic acid ethyl ester (21; 5.97 g, 0.016 mol) and SO$_2$Cl$_2$ (2.16 g, 0.016 mol) in CH$_2$Cl$_2$ (50 mL) gave 3-chloro-6-(4-chlorophenyl)-4-[(E)-methanesulfonyloximino]-1,4,5, 6-tetrahydropyridine-2-carboxylic acid ethyl ester (28; 6.43 g, 99%, 92% pure by $^1$H NMR) as a fluffy light yellow solid: 57-59° C.; $^1$H NMR (400 MHz, CDCl$_3$) δ 7.35 (m, 4H), 5.35 (s, 1H), 4.44 (dd, J=13.0, 3.2 Hz, 1H), 4.39 (t, J=7.1 Hz, 2H), 3.39 (ddd, J=16.9, 4.2, 1.8 Hz, 1H), 3.22 (s, 3H), 2.65 (dd, J=16.9, 13.9 Hz, 1H), 1.40 (t, J=7.1 Hz, 3H); HRMS-ESI (m/z): calcd for C$_{125}$H$_{16}$Cl$_2$N$_2$O$_5$S, 406.015. found, 406.016.

3-Chloro-6-(4-chloro-2-fluoro-3-methoxyphenyl)-4-[(E)-methanesulfonyloximino]-1,4,5,6-tetrahydropyridine-2-carboxylic acid methyl ester (29)

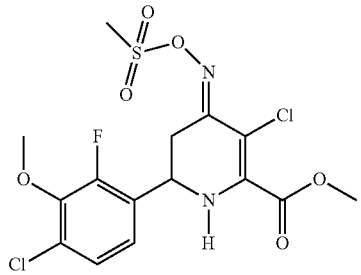

Using the procedure of Example 13, 6-(4-chloro-2-fluoro-3-methoxyphenyl)-4-[(E,Z)-methanesulfonyloximino]-1,4, 5,6-tetrahydropyridine-2-carboxylic acid methyl ester (23; 2.04 g, 0.005 mol) and SO$_2$Cl$_2$ (0.68 g, 0.005 mol) in CH$_2$Cl$_2$ (10 mL) gave 3-chloro-6-(4-chloro-2-fluoro-3-methoxyphenyl)-4-[(E)-methanesulfonyloximino]-1,4,5,6-tetrahydropyridine-2-carboxylic acid methyl ester (29; 2.18 g, 99%, 95% pure by $^1$H NMR) as a fluffy light yellow solid: mp 64-66° C.; $^1$H NMR (400 MHz, CDCl$_3$) δ 7.24 (dd, J=8.8, 1.3 Hz, 1H), 7.09 (dd, J=8.5, 6.7 Hz, 1H), 5.38 (s, 1H), 4.78 (dd, J=12.7, 4.5 Hz, 1H), 3.98 (s, 3H), 3.93 (s, 3H), 3.42 (dd, J=16.7, 4.5 Hz, 1H), 3.24 (s, 3H), 2.77 (dd, J=16.9, 12.8 Hz, 1H); HRMS-ESI (m/z): calcd for C$_{15}$H$_{15}$ClFN$_2$O$_5$S, 441.001. found, 441.002.

3-Chloro-6-(4-chloro-2-fluoro-3-methoxyphenyl)-4-[(E)-methanesulfonyloximino]-1,4,5,6-tetrahydropyridine-2-carboxylic acid ethyl ester (30)

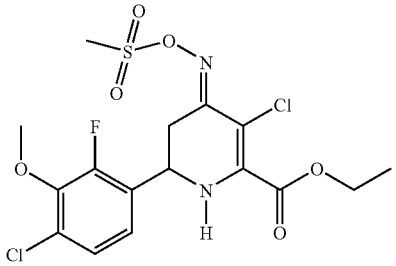

Using the procedure of Example 13, 6-(4-chloro-2-fluoro-3-methoxyphenyl)-4-[(E,Z)-methanesulfonyloximino]-1,4, 5,6-tetrahydropyridine-2-carboxylic acid methyl ester (25; 2.11 g, 0.005 mol) and SO$_2$Cl$_2$ (0.68 g, 0.005 mol) in CH$_2$Cl$_2$ (10 mL) gave 3-chloro-6-(4-chloro-2-fluoro-3-methoxyphenyl)-4-[(E)-methanesulfonyloximino]-1,4,5,6-tetrahydropyridine-2-carboxylic acid ethyl ester (30; 2.21 g, 97%, 95% pure by $^1$H NMR) as a fluffy light yellow solid: mp 60-62° C.; $^1$H NMR (400 MHz, CDCl$_3$) δ 7.21 (dd, J=8.5, 1.8 Hz, 1H), 7.08 (dd, J=8.6, 6.9 Hz, 1H), 5.32 (s, 1H), 4.78 (dd, J=12.8, 4.5 Hz, 1H), 4.41 (q, J=7.1 Hz, 2H), 3.99 (d, J=1.3 Hz, 3H), 3.41 (dd, J=16.9, 4.5 Hz, 1H), 3.23 (s, 3H), 2.76 (dd, J=11.7, 5.2 Hz, 1H), 1.40 (t, J=7.1 Hz, 3H); HRMS-ESI (m/z): calcd for $C_{16}H_{17}Cl_2FNO_6S$, 454.016. found, 454.017.

3-Chloro-6-(4-chloro-2-fluoro-3-methoxyphenyl)-4-[(E)-p-toluenesulfonyloximino]-1,4,5,6-tetrahydropyridine-2-carboxylic acid methyl ester (31)

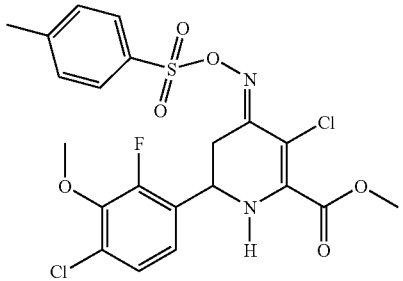

Using the procedure of Example 13, 6-(4-chloro-2-fluoro-3-methoxyphenyl)-4-[(E,Z)-p-toluenesulfonyloximino]-1,4,5,6-tetrahydropyridine-2-carboxylic acid methyl ester (22; 0.628 g, 0.0013 mol) and $SO_2Cl_2$ (0.175 g, 0.0013 mol) in $CH_2Cl_2$ (5 mL) gave 3-chloro-6-(4-chloro-2-fluoro-3-methoxyphenyl)-4-[(E)-p-toluenesulfonyloximino]-1,4,5,6-tetrahydropyridine-2-carboxylic acid methyl ester (31; 0.616 g, 98%, 95% pure by $^1H$ NMR) as a fluffy light yellow solid: mp 62-64° C.; $^1H$ NMR (400 MHz, $CDCl_3$) δ 7.91 (d, J=8.3 Hz, 2H), 7.34 (d, J=8.0 Hz, 2H), 7.16 (dd, J=8.5, 1.7 Hz, 1H), 7.01 (dd, J=8.4, 7.1 Hz, 1H), 5.25 (s, 1H), 4.70 (dd, J=12.6, 4.3 Hz, 1H), 3.97 (d, J=1.2 Hz, 3H), 3.91 (s, 3H), 3.33 (ddd, J=16.8, 4.4, 1.6 Hz, 1H), 2.88-2.64 (m, 1H), 2.45 (s, 3H); HRMS-ESI (m/z): calcd for $C_{21}H_{19}Cl_2FN_2O_5S$, 516.0322. found, 516.0319.

Example 14

Preparation of 3-bromo-6-(4-chloro-2-fluoro-3-methoxyphenyl)-4-[(E)-methanesulfonyloximino]-1,4,5,6-tetrahydropyridine-2-carboxylic acid methyl ester (32)

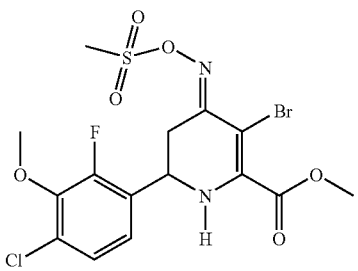

N-Bromosuccinimide (0.512 g, 2.88 mmol) was added to a solution of (6-(4-chloro-2-fluoro-3-methoxyphenyl)-4-[(E,Z)-methanesulfonyloximino]-1,4,5,6-tetrahydropyridine-2-carboxylic acid methyl ester (23; 1.17 g, 2.88 mmol) in $CH_2Cl_2$ (10 mL). The reaction mixture was stirred at ambient temperature for 1 h and it was then diluted with $CH_2Cl_2$ and washed with $H_2O$. The organic layer was separated and dried via Biotage Phase Separator SPE. The solvent was removed in vacuo to yield a brown oil (1.4 g). Purification by silica gel chromatography (40% EtOAc/10% $CH_2Cl_2$/50% pentane) provided 3-bromo-6-(4-chloro-2-fluoro-3-methoxyphenyl)-4-[(E)-methanesulfonyloximino]-1,4,5,6-tetrahydropyridine-2-carboxylic acid methyl ester (32; 1.17 g, 84%) as a yellow glass: $^1H$ NMR (300 MHz, $CDCl_3$) δ 7.21 (dd, J=8.6, 1.8 Hz, 1H), 7.07 (dd, J=8.4, 6.7 Hz, 1H), 5.39 (s, 1H), 4.81 (d, J=12.2 Hz, 1H), 4.01-3.97 (m, 4H), 3.94 (d, J=2.0 Hz, 3H), 3.43 (dd, J=16.8, 2.8 Hz, 1H), 3.23 (d, J=1.9 Hz, 3H), 2.79 (dd, J=16.8, 12.7 Hz, 1H); HRMS-ESI (m/z): calcd for $C_{15}H_{17}BrClFN_2O_6S$, 485.9663. found, 485.9663.

Example 15

Preparation of 3-chloro-6-(4-chloro-2-fluoro-3-methoxyphenyl)-4-oxo-1,4,5,6-tetrahydropyridine-2-carboxylic acid methyl ester (33)

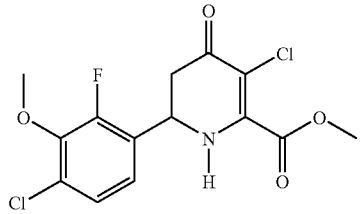

6-(4-Chloro-2-fluoro-3-methoxyphenyl)-4-oxo-1,4,5,6-tetrahydropyridine-2-carboxylic acid methyl ester (16; 483 mg, 1.54 mmol) was slurried in $CH_2Cl_2$ (10 mL) and cooled in an ice bath. A solution of $SO_2Cl_2$ (209 mg, 1.55 mmol) in $CH_2Cl_2$ (5 mL) was added dropwise. After 30 min, the reaction solution was quenched with 10% aqueous sodium bisulfite solution. The organic layer was separated, washed with saturated aqueous $NaHCO_3$ solution, $H_2O$ and brine and then dried ($MgSO_4$). The solution was evaporated to a yellow oil which was crystallized from cold methanol to give 3-chloro-6-(4-chloro-2-fluoro-3-methoxyphenyl)-4-oxo-1,4,5,6-tetrahydropyridine-2-carboxylic acid methyl ester (33; 0.437 g, 81%) as a light yellow solid: mp 127-129° C.; $^1H$ NMR (300 MHz, $CDCl_3$) δ 7.20 (dd, $J_{F-H}$=1.5 Hz, $J_{H-H}$=8.1 Hz, 1H, aromatic), 7.10 (dd, $J_{F-H}$=6.9 Hz, $J_{H-H}$=8.1 Hz, 1H, aromatic), 5.82 (br s, 1H, NH), 5.10 (t, J=9.3 Hz, 1H, H6), 3.98 (d, $J_{F-H}$=1.5 Hz, 3H, $OCH_3$), 3.97 (s, 3H, $CO_2CH_3$), 2.88 (d, J=9 Hz, 2H, H5); ESIMS m/z 347.9 ([M+H]$^+$).

Example 16

Preparation of 3-chloro-6-(4-chloro-2-fluoro-3-methoxyphenyl)-4-hydroxyimino-1,4,5,6-tetrahydropyridine-2-carboxylic acid methyl ester (34)

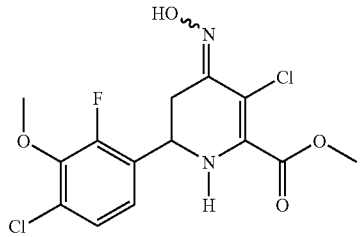

3-Chloro-6-(4-chloro-2-fluoro-3-methoxyphenyl)-3-chloro-4-oxo-1,4,5,6-tetrahydropyridine-2-carboxylic acid methyl ester (33; 1.612 g, 4.63 mmol) was suspended in MeOH (20 mL). Hydroxylamine hydrochloride (966 mg, 13.9 mmol) was added followed by pyridine (3 mL). The reaction mixture was stirred for 18 h at room temperature and then for 4 h at 40° C. The solvent was removed by rotary evaporation. H$_2$O (100 mL) was added, and the resulting solid was filtered, washed with H$_2$O followed by MeOH to give 3-chloro-6-(4-chloro-2-fluoro-3-methoxyphenyl)-4-hydroxyimino-1,4,5,6-tetrahydropyridine-2-carboxylic acid methyl ester (34; 1.353 g, 81%) as a white powder: mp 174-176° C.; $^1$H NMR (300 MHz, DMSO-d$_6$) δ 11.23 (s, 1H, NOH), 7.35 (dd, J$_{F-H}$=1.5 Hz, J$_{H-H}$=8.7 Hz, 1H, aromatic), 7.17 (dd, J$_{F-H}$=J$_{H-H}$=8.7 Hz, 1H, aromatic), 6.93 (br s, 1H, NH), 4.69 (m, 1H, H6), 3.88 (s, 3H), 3.79 (s, 3H), 3.03 (dd, J=4.5, 16 Hz, 1H, H5a), 2.74 (dd, J=9.0, 16 Hz, 1H, H5b); Anal. Calcd for C$_{14}$H$_{13}$Cl$_2$FN$_2$O$_4$: C, 46.30; H, 3.61; N, 7.71. Found: C, 46.77; H, 3.64; N, 7.42.

Example 17

Preparation of 3-chloro-6-(4-chloro-2-fluoro-3-methoxyphenyl)-4-[(E)-acetoxyoximino]-3-chloro-1,4,5,6-tetrahydropyridine-2-carboxylic acid methyl ester (35)

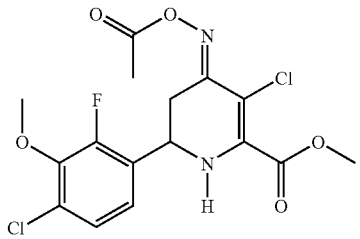

3-Chloro-6-(4-chloro-2-fluoro-3-methoxyphenyl)-3-chloro-4-hydroxyimino-1,4,5,6-tetrahydropyridine-2-carboxylic acid methyl ester (34, 756 mg, 2.08 mmol) was slurried in glacial acetic acid (10 mL). Acetic anhydride (241 mg, 2.36 mmol) was added dropwise at room temperature. The reaction mixture was heated at 80° C. for 2 h. The solution was concentrated under vacuum, and the residue was dissolved in CH$_2$Cl$_2$ (50 mL) and washed with saturated aqueous NaHCO$_3$ solution. The extracts were washed with brine, dried (MgSO$_4$) and evaporated to give 3-chloro-6-(4-chloro-2-fluoro-3-methoxyphenyl)-4-[(E)-acetoxyoximino]-3-chloro-1,4,5,6-tetrahydropyridine-2-carboxylic acid methyl ester (35; 842 mg, 99%) as a light orange solid: $^1$H NMR (400 MHz, CDCl$_3$) δ 7.21 (dd, J$_{F-H}$=1.5 Hz, J$_{H-H}$=8.4 Hz, 1H, aromatic), 7.11 (dd, J$_{F-H}$=6.9 Hz, J$_{H-H}$=8.4 Hz, 1H, aromatic), 5.24 (br s, 1H, NH), 4.76 (dd, J=4.2, 12.3 Hz, 1H, H5$_a$), 3.98 (d, J$_{F-H}$=1.5 Hz, 3H, OMe), 3.94 (s, 3H, CO$_2$Me), 3.40 (ddd, J$_{F-H}$=1.8 Hz, J$_{H-H}$=4.2, 16.5 Hz, 1H, H6), 2.72 (dd, J=12.3, 16.5 Hz, 1H, H5$_b$), 2.23 (s, 3H, NOAc). HRMS calcd for C$_{16}$H$_{15}$Cl$_2$FN$_2$O$_5$: 404.034. Found: 404.034.

Example 18

Preparation of 4-amino-3-chloro-6-(4-chloro-2-fluorophenyl)pyridine-2-carboxylic acid ethyl ester (36)

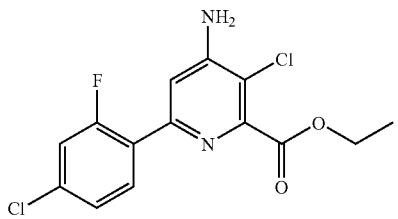

Step 1. A solution of (2Z,5E)-2-amino-6-(4-chloro-2-fluorophenyl)-4-oxo-hexa-2,5-dienoic acid ethyl ester (7; 6.0 g, 0.02 mol) in anhydrous 1,4-dioxane (100 mL) was heated to 185° C. in a 200 mL Parr reactor under a positive N$_2$ pressure. After 14 h, the reactor was cooled, and the solvent was removed under reduced pressure leaving a dark orange oil (7.1 g). By $^1$H NMR spectroscopy the material was 90% of the desired 6-(4-chloro-2-fluorophenyl)-4-oxo-1,4,5,6-tetrahydropyridine-2-carboxylic acid ethyl ester (11).

Step 2. A mixture of the above material and 50% aqueous hydroxylamine (4.0 g) in toluene (150 mL) was heated to reflux for 4 h. The reaction mixture was cooled to room temperature and CH$_2$Cl$_2$ (150 mL) was added. The organic layer was washed with a saturated solution of NaCl and dried (MgSO$_4$). Solvent removal gave a mixture of isomers of 6-(4-chloro-2-fluorophenyl)-4-hydroxyimino-1,4,5,6-tetrahydropyridine-2-carboxylic acid ethyl ester (17, 4.3 g) as a brown solid.

Step 3. The above material was dissolved in glacial acetic acid (30 mL), the mixture was cooled to 5° C., and a solution of SO$_2$Cl$_2$ (4.05 g, 0.03 mol) in glacial acetic acid (5 mL) was added over 10 min. After 5 d at room temperature, the solvent was removed on the rotary evaporator, and the residue was dissolved in CH$_2$Cl$_2$ (100 mL). After washing the solution with a saturated solution of NaHCO$_3$ and drying (MgSO$_4$), solvent removal gave an orange oil (4.6 g) that contained 65% of 4-amino-3-chloro-6-(4-chloro-2-fluorophenyl)pyridine-2-carboxylic acid ethyl ester by $^1$H NMR. Silica gel column chromatography (20% EtOAc/hexanes) gave compound 36 (2.2 g, 33% over 3 steps) as an off-white solid: mp 109-110° C.; $^1$H NMR (400 MHz, CDCl$_3$) δ 7.96 (t, J=8.5 Hz, 1H), 7.20 (dd, J=8.4, 1.7 Hz, 1H), 7.16 (d, J=1.4 Hz, 1H), 7.13 (dd, J=11.1, 2.0 Hz, 1H), 4.91 (s, 2H), 4.47 (q, J=7.1 Hz, 2H), 1.43 (t, J=7.1 Hz, 3H); Anal. C$_{14}$H$_{11}$Cl$_2$FN$_2$O$_2$: C, 51.09; H, 3.37; N, 8.51. Found: C, 50.90; H, 3.31; N, 8.47.

Example 19

Preparation of 4-amino-3-chloro-6-(4-chlorophenyl)pyridine-2-carboxylic acid ethyl ester (37)

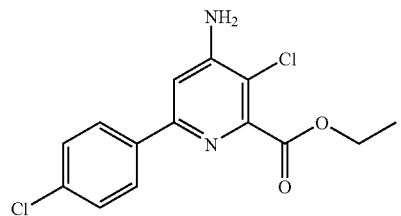

To a magnetically stirred solution of 6-(4-chlorophenyl)-4-hydroxyimino-1,4,5,6-tetrahydropyridine-2-carboxylic acid ethyl ester (19; 0.589 g, 0.002 mol) in glacial acetic acid (5 mL) cooled to 5° C. was added SO$_2$Cl$_2$ (0.16 mL, 0.002 mol). After warming to room temperature for 2 h, additional SO$_2$Cl$_2$ (0.225 mL, 0.0028 mol) was added. After 2 d at room temperature, solvent was removed on the rotary evaporator and the residue was dissolved in CH$_2$Cl$_2$ (50 mL). After washing the solution with a saturated solution of NaHCO$_3$ and drying (MgSO$_4$), solvent removal gave a light yellow solid (0.65 g). Preparative thin layer silica gel chromatography (20% EtOAc/hexanes) gave 4-amino-3-chloro-6-(4-chlorophenyl)-pyridine-2-carboxylic acid ethyl ester (37; 0.325 g, 52%, 93% pure by $^1$H NMR) as a white solid: mp 128-130° C.; ¹H NMR (400 MHz, CDCl₃) δ 7.90-7.82 (m, 2H), 7.46-7.36 (m, 2H), 7.07 (s, 1H), 4.81 (s, 2H), 4.48 (q, J=7.1 Hz, 2H), 1.44 (t, J=7.1 Hz, 3H); HRMS-ESI (m/z): calcd for C₁₄H₁₂Cl₂N₂O₂, 310.027. found, 310.028. Also collected was 4-amino-3,5-dichloro-6-(4-chlorophenyl)pyridine-2-carboxylic acid ethyl ester (38; 0.092 g, 13% yield) as a white solid: mp 143-145° C.; ¹H NMR (400 MHz, CDCl₃) δ 7.73-7.58 (m, 2H), 7.49-7.36 (m, 2H), 5.31 (s, 2H), 4.45 (q, J=7.1 Hz, 2H), 1.41 (t, J=7.1 Hz, 3H); HRMS-ESI (m/z): calcd for C₁₄H₁₁Cl₃N₂O₂, 344.013. found, 344.013.

Example 20

Preparation of 4-amino-3-chloro-6-(4-chloro-2-fluoro-3-methoxy-phenyl acid methyl ester (39)

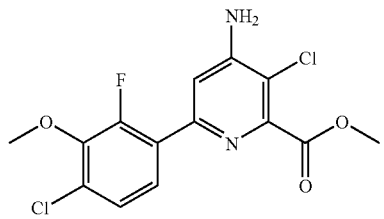

3-Chloro-6-(4-chloro-2-fluoro-3-methoxyphenyl)-4-[(Z)-hydroxyimino]-1,4,5,6-tetrahydropyridine-2-carboxylic acid methyl ester (18, 756 mg, 2.08 mmol) was slurried in glacial acetic acid (10 mL). Acetic anhydride (241 mg, 2.36 mmol) was added dropwise at room temperature. The reaction mixture was stirred at reflux under nitrogen for 6 h. The solution was concentrated under vacuum. The residue was dissolved in CH₂Cl₂ (50 mL) and washed with saturated aqueous NaHCO₃ solution. The extracts were washed with brine, dried (MgSO₄) and evaporated to a brown solid. Purification using silica gel chromatography with a hexane-EtOAc gradient gave 4-amino-3-chloro-6-(4-chloro-2-fluoro-3-methoxy-phenyl)pyridine-2-carboxylic acid methyl ester (39; 0.204 g, 28%) as a tan solid: ¹H NMR (400 MHz, CDCl₃) δ 7.65 (dd, J=8.6, 7.8 Hz, 1H), 7.23 (dd, J=8.7, 1.8 Hz, 1H), 7.18 (d, J=1.7 Hz, 1H), 4.85 (s, 2H), 4.00 (s, 3H), 3.97 (d, J=0.9 Hz, 3H).); HRMS-ESI (m/z): calcd for C₁₄H₁₁Cl₂FN₂O₃, 344.013. found, 344.013.

Example 21

Preparation of 4-amino-3-chloro-6-(4-chloro-2-fluoro-3-methoxy-phenyl acid methyl ester (39)

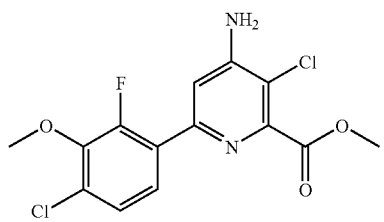

A magnetically stirred solution of 6-(4-chloro-2-fluoro-3-methoxyphenyl)-4-[(E)-methanesulfonyloximino]-3-chloro-1,4,5,6-tetrahydropyridine-2-carboxylic acid methyl ester (29, 0.441 g (0.001 mol) in glacial acetic acid (2 mL) was warmed to 90° C. for 4 h. After removing the solvent on the rotary evaporator, the residue was dissolved in CH₂Cl₂ (25 mL) and was washed with saturated solutions of NaHCO₃ and NaCl. After drying (MgSO₄), solvent removal gave 4-amino-3-chloro-6-(4-chloro-2-fluoro-3-methoxyphenyl)pyridine-2-carboxylic acid methyl ester (39; 0.332 g, 96%; 93% pure by GC and ¹H NMR spectroscopy) as a white solid: mp 141-143° C. ¹H NMR (400 MHz, CDCl₃) δ 7.65 (dd, J=8.6, 7.8 Hz, 1H), 7.23 (dd, J=8.7, 1.8 Hz, 1H), 7.18 (d, J=1.7 Hz, 1H), 4.85 (s, 2H), 4.00 (s, 3H), 3.97 (d, J=0.9 Hz, 3H). HRMS-ESI (m/z): calcd for C₁₄H₁₁Cl₂FN₂O₃, 344.013. found, 344.013.

Example 22

Preparation of 4-amino-3-chloro-6-(4-chloro-2-fluoro-3-methoxyphenyl)pyridine-2-carboxylic acid ethyl ester (40)

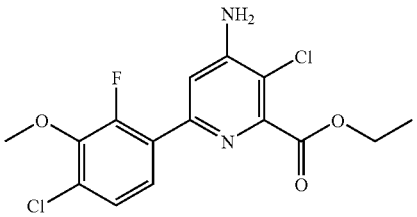

To a magnetically stirred solution of 6-(4-chloro-2-fluoro-3-methoxyphenyl)-4-[(E,Z)-methanesulfonyloximino]-1,4,5,6-tetrahydropyridine-2-carboxylic acid ethyl ester (25, 4.20 g, 0.01 mol) in glacial acetic acid (100 mL) cooled to 5° C. was added a solution of SO₂Cl₂ (1.35 g, 0.01 mol) in glacial acetic acid (3 mL) over 5 min. The reaction mixture was warmed to room temperature for 1 h, then to 90° C. for 4 h. After removing the solvent on the rotary evaporator, the residue was dissolved in CH₂Cl₂ (100 mL) and was washed with saturated solutions of NaHCO₃ and NaCl. After drying (MgSO₄), solvent removal gave a yellow solid (3.55 g) that contained 81% of 4-amino-3-chloro-6-(4-chloro-2-fluoro-3-methoxyphenyl)pyridine-2-carboxylic acid ethyl ester (40) by ¹H NMR spectroscopy. Silica gel column chromatography (20% EtOAc/hexanes) gave the product as an off-white solid (2.75 g, 78%, 93% pure by GC and ¹H NMR spectroscopy): mp 73-74° C.; ¹H NMR (400 MHz, CDCl₃) δ 7.67 (dd, J=8.6, 7.8 Hz, 1H), 7.23 (dd, J=8.7, 1.7 Hz, 1H), 7.18 (d, J=1.7 Hz, 1H), 4.83 (s, 2H), 4.48 (q, J=7.1 Hz, 2H), 3.97 (d, J=0.8 Hz, 3H), 1.43 (t, J=7.1 Hz, 3H); HRMS-ESI (m/z): calcd for C₁₅H₁₃Cl₂FN₂O₃, 358.028. found, 358.059.

Example 23

Preparation of 4-amino-3-bromo-6-(4-chloro-2-fluorophenyl)pyridine-2-carboxylic acid methyl ester (41)

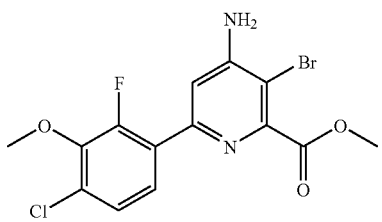

A solution of 3-bromo-6-(4-chloro-2-fluoro-3-methoxyphenyl)-4-[(E)-methylsulfonyloximino]-1,4,5,6-tetrahydropyridine-2-carboxylic acid methyl ester (23, 900 mg, 1.856 mmol) in glacial acetic acid (4.6 mL) was heated at 150° C. for 5 min in a Biotage microwave. After cooling to ambient temperature the reaction mixture was diluted with H$_2$O and the pH was made neutral with a saturated solution of Na$_2$CO$_3$. The resulting mixture was extracted 3 times with ethyl acetate. The combined organic extracts were washed with brine, dried with Na$_2$SO$_4$, filtered and concentrated in vacuo. Silica gel column chromatography (20% EtOAc/pentane) gave 4-amino-3-bromo-6-(4-chloro-2-fluorophenyl)pyridine-2-carboxylic acid methyl ester (41; 0.60 g, 83%) as a light brown solid: mp 148-149° C.; $^1$H NMR (300 MHz, CDCl$_3$) δ 7.65 (dd, J=8.6, 7.7 Hz, 1H), 7.26-7.20 (m, 1H), 7.14 (d, J=1.8 Hz, 1H), 4.91 (s, 2H), 3.99 (s, 3H), 3.97 (d, J=0.9 Hz, 3H); HRMS-ESI (m/z): calcd for C$_{14}$H$_{11}$BrClFN$_2$O$_3$, 387.962. found, 387.963.

What is claimed is:

1. A process for the preparation of a 6-(aryl)-4-aminopicolinate of the formula

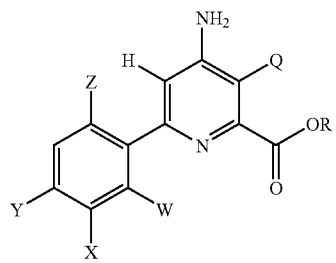

wherein

Q represents Cl or Br;

R represents C$_1$-C$_4$ alkyl; and

W represents H, F or Cl;

X represents H, F, C$_1$ or C$_1$-C$_4$ alkoxy;

Y represents halogen; and

Z represents H or F;

which comprises heating a 3-halo-6-(aryl)-4-iminotetrahydropicolinic acid ester of Formula (I)

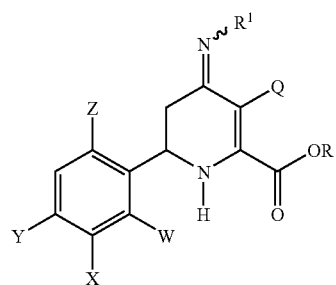

wherein

R represents C$_1$-C$_4$ alkyl;

R$^1$ represents —OS(O)$_2$R$^2$, —OC(O)R$^2$ or —OC(O)OR$^2$;

R$^2$ represents C$_1$-C$_4$ alkyl or unsubstituted or substituted phenyl;

Q represents Cl or Br; and

W represents H, F or Cl;

X represents H, F, C$_1$ or C$_1$-C$_4$ alkoxy;

Y represents halogen; and

Z represents H or F;

at a temperature from about 25° C. to about 150° C. in the presence of a polar solvent and recovering the product.

2. The process of claim 1 in which the polar solvent is a C$_1$-C$_4$ alkanoic acid.

3. The process of claim 1 in which the 3-halo-6-(aryl)-4-iminotetrahydropicolinic acid ester is prepared by chlorinating or brominating a sulfonylated, acylated or carbonate-containing oxime of the formula

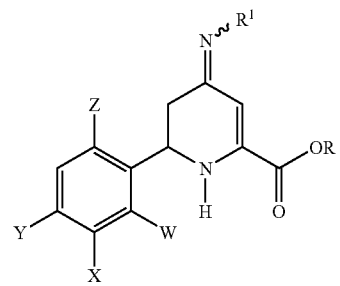

wherein W, X, Y, Z, R, R$^1$ and R$^2$ are as previously defined with a chlorinating or brominating agent.

* * * * *